US009980499B2

(12) United States Patent
Fremaux et al.

(10) Patent No.: US 9,980,499 B2
(45) Date of Patent: *May 29, 2018

(54) STREPTOCOCCUS THERMOPHILUS LACTIC ACID BACTERIUM

(71) Applicant: DUPONT NUTRITION BIOSCIENCES APS, Postboks (DK)

(72) Inventors: Christophe Fremaux, Poitiers (FR); Philippe Horvath, Saint-Gervais-les-3-Clochers (FR); Joachim Schwobe, Niebüll (FR)

(73) Assignee: DUPONT NUTRITION BIOSCIENCES APS (DK)

( * ) Notice: Subject to any disclaimer, the term of this patent is extended or adjusted under 35 U.S.C. 154(b) by 503 days.

This patent is subject to a terminal disclaimer.

(21) Appl. No.: 14/478,969

(22) Filed: Sep. 5, 2014

(65) Prior Publication Data

US 2015/0201634 A1 Jul. 23, 2015

Related U.S. Application Data

(63) Continuation of application No. 12/304,913, filed as application No. PCT/IB2007/002639 on Jun. 8, 2007, now abandoned.

(60) Provisional application No. 60/804,978, filed on Jun. 16, 2006.

(51) Int. Cl.
| | |
|---|---|
| *A23C 9/123* | (2006.01) |
| *A23C 19/00* | (2006.01) |
| *A23C 19/032* | (2006.01) |
| *C07K 14/315* | (2006.01) |
| *C12R 1/46* | (2006.01) |
| *C12N 15/74* | (2006.01) |
| *A23K 10/12* | (2016.01) |
| *A23K 10/18* | (2016.01) |
| *A23L 33/135* | (2016.01) |
| *A23C 13/16* | (2006.01) |

(52) U.S. Cl.
CPC ........... *A23C 9/1238* (2013.01); *A23C 13/16* (2013.01); *A23C 19/00* (2013.01); *A23C 19/0323* (2013.01); *A23K 10/12* (2016.05); *A23K 10/18* (2016.05); *A23L 33/135* (2016.08); *C07K 14/315* (2013.01); *C12N 15/746* (2013.01); *C12R 1/46* (2013.01); *A23V 2002/00* (2013.01); *A23Y 2240/75* (2013.01)

(58) Field of Classification Search
CPC ..... A23C 13/16; A23C 19/00; A23C 19/0323; A23C 9/1238; A23K 10/12; A23K 10/18; A23L 33/135; A23L 3/3526; A23L 3/375; A23L 13/424; A23L 13/426; A23L 1/31427; A23L 27/26; A23L 2/44; A23V 2002/00; A23Y 2240/75; C07K 14/315; C12N 15/746; C12R 1/46; A23B 7/154; A23B 7/055; A23B 4/20; A23B 5/14; A23B 9/26; A01N 1/02; A01N 1/0221

See application file for complete search history.

(56) References Cited

U.S. PATENT DOCUMENTS

2006/0240539 A1 10/2006 Horvath et al.

FOREIGN PATENT DOCUMENTS

| | | |
|---|---|---|
| EP | 1016709 | 4/2005 |
| WO | WO 99/62316 | 12/1999 |
| WO | WO 01/16329 | 3/2001 |
| WO | WO 2004/085607 | 10/2004 |
| WO | WO 07/025097 | 3/2007 |
| WO | WO 2007/095958 | 8/2007 |

OTHER PUBLICATIONS

GenBank DQ073002 Streptococcus thermophilus strain Jim 72 CRISRP repeat sequence Aug. 1, 2005.
GenBank DQ073004 Streptococcus thermophilus strain CNRZ 1205 CRISRP repeat sequence Aug. 1, 2005.
GenBank DQ073005 Streptococcus thermophilus strain 1205.3 Crisrp repeat sequence Aug. 1, 2005.
Foley, Cophey, et al. "A short noncoding viral DNA element showing characteristics of replication origi confers bacteriophage resistance of Streptococcus thermophilus," Virology (1998) vol. 25:2 pp. 377-387.
Forde, Amanda, et al., "Bacteriophage defense systems in lactic acid bacteria," Antonie van leeuwenhoek, Dordrecht, NL (1999) vol. 76: 1-4 pp. 89-113.
Coffey A., et al., "Bacteriophage-resistance system in dairy starter strains: Molecular analysis to application," Antoine Can Leeuwenheok, Kluwer Academic Publishers (2002) vol. 82: 1-2 pgs.
Viscardi, M., et al., "Selection of bacteriophage-resistant mutants of Streptoccus thermophilus," Journal of Microbiological Methods (2003) vol. 55L1, pp. 109-119.
Farber E. J., et al., "The expopolysaccharides produced by Streptococcus thermophilus Rs and Sts have the same repeating unti but differ in viscosity of their milk cultures," Carbohydrate Resaerch, Eliseveir Scientific Publishiung Company (1998) vol. 310:4 pgs.
"Streptococcus thermophilus strain CNRZ 385 CRISPR repeat sequence," XP002464697 (Aug. 2, 2005).
Bolotin, Alexander, et al., "Clustered regularly interspaces short palindrome repeats (CR1SPRs) have spacers of extrachromosoma," Micorbiology (2005) vol. 151 No. 8, pp. 2551-2561.
"Streptococcus thennophilus strain MTC31 0 expolysaccharide synthesis gene cluster, partial sequence," XP002464696 (Aug. 16, 2002).
Broadbent J. R., et al., "Biochemistry, genetics, and applications of exopolysaccharide production in Streptococcus thennophilus: a review," Journal of Dairy Science, American Dairy Science Association (2003) vol. 86:2, pp. 407-423.

(Continued)

Primary Examiner — Debbie K Ware

(57) ABSTRACT

The disclosure relates in one aspect to a fast acidifying lactic acid bacterium that generates a viscosity in fermented milk greater than about 62 Pa·s after 14 days of storage at 6° C. Further, the disclosure includes method for preparing and products of food, food additive, feed, nutritional supplement, or probiotic supplement, thereof.

20 Claims, 3 Drawing Sheets

(56) References Cited

OTHER PUBLICATIONS

Sebastiani, H., "Saurewecker LF7—Produktspezif1kation" Bundesanstalt Fur Alpenlandische Milchwirtschaft, XP002464695 (Dec. 5, 2007) http://www.bam-rotholz.at/dokumente/ms/bkulturen/lf7kulturen sp.pdf [retreived Jan. 15, 2008).

Sebastiani, H., "Saurewecker LF7—Zuchtungsanleitung" Bundesanstalt Fur Alpenlandische Milchwirtschaft, XP002464694 (Jan. 27, 2005) http://www.bam-rotholz.at/dokumente/ms/bkulturen/lf7kulturen a.pdf [retreived Jan. 15, 2008].

Sebastiani, H., "Streptococcenkultur EP27—Produktspezif1kation" Bundesanstalt Fur Alpenlandische Milchwirtschaft, XP002444403 (Dec. 18, 2006) http://www.bam-rotholz.at/dokumente/ms/bkulturen/ep27kulturen sp.pdf [retreived Jul. 26, 2008].

Sebastiani, H., "Streptococcenkultur EP27—Zuchtungsanleitung" Bundesanstalt Fur Alpenlandische Milchwirtschaft, XP002444404 (Jan. 27, 2005) http://www.bam-rotholz.at/dokumente/ms/bkulturen/ep27kulturen a.pdf [retreived on Jul. 26, 2007].

FIGURE 3

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|---|---|---|---|---|---|---|---|---|---|---|---|---|---|
| DSMZ18344 | x | x | C | D | E | F | G | H | I | x | x | x | M | N | O | P | Q | R | S | S | T | | | | | | | | | | | |
| CNCM I-2425 | A | B | C | D | E | F | G | H | I | J | K | L | M | N | O | P | Q | R | S | x | T | | | | | | | | | | | |
| CNRZ385 | A | B | C | D | E | F | G | H | I | J | K | L | M | N | O | P | Q | R | S | x | T | | | | | | | | | | | |
| CNCM I-2423 | U1 | U2 | U3 | U4 | U5 | U6 | U7 | U8 | U9 | U10 | U11 | U12 | U13 | U14 | U15 | U16 | U17 | U18 | U19 | U20 | U21 | U22 | U23 | U24 | U25 | U26 | U27 | U28 | U29 | U30 | U31 | U32 |

SEQUENCE LISTING

<160> NUMBER OF SEQ ID NOS: 24

<210> SEQ ID NO 1
<211> LENGTH: 37
<212> TYPE: DNA
<213> ORGANISM: Streptococcus thermophilus

<400> SEQUENCE: 1
actatgtggg tataaaaaca tcaaaatttc atttgag                         37

<210> SEQ ID NO 2
<211> LENGTH: 30
<212> TYPE: DNA
<213> ORGANISM: Streptococcus thermophilus

<400> SEQUENCE: 2
aatatctaca ggtcactaca aagctacgct                                 30

<210> SEQ ID NO 3
<211> LENGTH: 30
<212> TYPE: DNA
<213> ORGANISM: Streptococcus thermophilus

<400> SEQUENCE: 3
gttggggtgt gtttgtaacg gcgtatgcta                                 30

<210> SEQ ID NO 4
<211> LENGTH: 30
<212> TYPE: DNA
<213> ORGANISM: Streptococcus thermophilus

<400> SEQUENCE: 4
tcaatcaggt gacggtgatg cttatattaa                                 30

<210> SEQ ID NO 5
<211> LENGTH: 30
<212> TYPE: DNA
<213> ORGANISM: Streptococcus thermophilus

<400> SEQUENCE: 5
catacatgat agtttgtcaa cacttttgat                                 30

<210> SEQ ID NO 6
<211> LENGTH: 30
<212> TYPE: DNA
<213> ORGANISM: Streptococcus thermophilus

<400> SEQUENCE: 6
tcagcatttg gtttacatga cccacgtctg                                 30

<210> SEQ ID NO 7
<211> LENGTH: 30
<212> TYPE: DNA
<213> ORGANISM: Streptococcus thermophilus

<400> SEQUENCE: 7
caatcaacag gtttgactga ttataacggt                                 30

<210> SEQ ID NO 8
<211> LENGTH: 30
<212> TYPE: DNA
<213> ORGANISM: Streptococcus thermophilus

<400> SEQUENCE: 8
tagctacaca tgaattttat tacaatggtg                                 30

<210> SEQ ID NO 9
<211> LENGTH: 30
<212> TYPE: DNA
<213> ORGANISM: Streptococcus thermophilus

<400> SEQUENCE: 9
ccgttcttca aacgttaaat tccaaggtgt                                                30

<210> SEQ ID NO 10
<211> LENGTH: 30
<212> TYPE: DNA
<213> ORGANISM: Streptococcus thermophilus

<400> SEQUENCE: 10
gctgcgatta tgacaatgct gtctgtaagg                                                30

<210> SEQ ID NO 11
<211> LENGTH: 30
<212> TYPE: DNA
<213> ORGANISM: Streptococcus thermophilus

<400> SEQUENCE: 11
gaagaattta ttaataaaga tggttctgct                                                30

<210> SEQ ID NO 12
<211> LENGTH: 30
<212> TYPE: DNA
<213> ORGANISM: Streptococcus thermophilus

<400> SEQUENCE: 12
aggcagaaaa gaagtatttt ggtaagtatg                                                30

<210> SEQ ID NO 13
<211> LENGTH: 29
<212> TYPE: DNA
<213> ORGANISM: Streptococcus thermophilus

<400> SEQUENCE: 13
aaatggttta tcgacaagaa aatgaagct                                                 29

<210> SEQ ID NO 14
<211> LENGTH: 30
<212> TYPE: DNA
<213> ORGANISM: Streptococcus thermophilus

<400> SEQUENCE: 14
ccaaatttgc attatacaaa acgctccttc                                                30

<210> SEQ ID NO 15
<211> LENGTH: 30
<212> TYPE: DNA
<213> ORGANISM: Streptococcus thermophilus

<400> SEQUENCE: 15
atcctaactg ctttgctaac tacatcatgg                                                30

<210> SEQ ID NO 16
<211> LENGTH: 30
<212> TYPE: DNA
<213> ORGANISM: Streptococcus thermophilus

<400> SEQUENCE: 16
atcctaactg ctttgctgac tacatcatgg                                                30

<210> SEQ ID NO 17
<211> LENGTH: 30
<212> TYPE: DNA
<213> ORGANISM: Streptococcus thermophilus

<400> SEQUENCE: 17
taacaagata agattagtcg tcttctacat                                       30

<210> SEQ ID NO 18
<211> LENGTH: 41
<212> TYPE: DNA
<213> ORGANISM: Streptococcus thermophilus

<400> SEQUENCE: 18
ttgattcaac ataaaaagcc agttcaattg aacttggctt t                          41

<210> SEQ ID NO 19
<211> LENGTH: 1169
<212> TYPE: DNA
<213> ORGANISM: Streptococcus thermophilus

<400> SEQUENCE: 19
actatgtggg tataaaaaca tcaaaatttc atttgaggtt tttgtactct caagatttaa      60
gtaactgtac aacaatatct acaggtcact acaaagctac gctgttttg tactctcaag      120 atttaagtaa ctgtacaacg ttggggtgtg tttgtaacgg cgtatgctag tttttgtact     180
ctcaagattt aagtaactgt acaactcaat caggtgacgg tgatgcttat attaagtttt     240
tgtactctca agatttaagt aactgtacaa ccatacatga gtttgtca cacttttga       300 tgttttgta ctctcaagat ttaagtaact gtacaactca gcatttggtt tacatgaccc      360
acgtctggtt tttgtactct caagatttaa gtaactgtac aaccaatcaa caggtttgac      420
tgattataac ggtgtttttg tactctcaag atttaagtaa ctgtacaact agctacacat      480
gaattttatt acaatggtgg ttttgtact ctcaagattt aagtaactgt acaacccgtt      540
cttcaaacgt taaattccaa ggtgtgtttt tgtactctca agatttaagt aactgtacaa      600
cgctgcgatt atgacaatgc tgtctgtaag ggtttttgta ctctcaagat ttaagtaact      660
gtacaacgaa gaatttatta ataaagatgg ttctgctgtt tttgtactct caagatttaa      720
gtaactgtac aacaggcaga aaagaagtat tttggtaagt atggttttg tactctcaag      780 atttaagtaa ctgtacaaca aatggtttat cgacaagaaa atgaagctgt ttttgtactc      840
tcaagattta agtaactgta caacccaaat ttgcattata caaaacgctc cttcgttttt      900
gtactctcaa gatttaagta actgtacaac atcctaactg ctttgctaac tacatcatgg      960 gttttttgtac tctcaagatt taagtaactg tacaacatcc taactgcttt gctgactaca     1020
tcatgggttt ttgtactctc aagatttaag taactgtaca actaacaaga taagattagt     1080
cgtcttctac atgttttttgt actctcaaga tttaagtaac tgtacagttt gattcaacat    1140
aaaaagccag ttcaattgaa cttggcttt                                       1169

<210> SEQ ID NO 20
<211> LENGTH: 17387
<212> TYPE: DNA
<213> ORGANISM: Streptococcus thermophilus

<400> SEQUENCE: 20
gctgagccag cttactagcg tacaggcacc tactaaggtt gataagaaca atatcgaggt      60
cttgatgtca gctctcaaaa aagataaaaa agttgatgtt aaagttgatg atgttgcttc     120
atatcaagaa gctatgata atctcaagtc tggcaaatct aaagctatgg tcttgagtgg     180
ctcttatgct agcctattag agtctgtcaa tagtaacctt gcttcaaatc taaaaacaat     240
ttatacttat aaaattaaaa agaagaataa caactctgca aaccaagtag attcaaaagt     300

-continued

```
cttcaatatt tatattagtg gtattgatac ctacggttcg atttcaacag tgtcacgttc       360
agatgtcaat attattatga cagtaaacat gaatacacat aagattctct tgacgactac       420
tccacgtgat gcatacgtta agattcctgg tggtggggca aaccagtatg ataaattaac       480
ccacgcaggt atttatggtg ttgaaacatc tgaacaaact ctggaagatc tatatggtac       540
taagattgat tactatgcac gaattaactt cacatctttc cttaagttga ttgaccaact       600
tggtggtgtg acagtccata atgatcaagc tttcacaagt cttcatggga agtttgattt       660
cccagttgga gatatccaaa tgaattcaga gcaagcactt ggatttgttc gtgaacgcta       720
tagtttagat ggcggagata atgaccgtgg taaaaaccag gagaaagtca tttctgcgat       780
tgtaaacaag ttggcttctc taaagtctgt atcaaacttt acttcaatcg ttaataatct       840
ccaagactct gttcagacaa atatttcttt ggataccatt aatgctttgg ctaatacaca       900
acttgattca ggctctaaat ttacagtaac gtctcaagca gtaactggta caggttcaac       960
cggacaattg acctcttatg cgatgccaaa ttctagtctt tacatgatga aactagataa      1020
ttcgagtgtg gcaagtgcct ctcaagctat caaaaatctg atggaggaaa ataagtgat       1080 tgacgttcac tcacatattg ttttttgatgt tgatgatggt cctaaaactt tagaagaaag      1140
tttagacctc attggtgaaa gttatgccca ggggtacgt aagattgttt caacatccca       1200
tcgtcgtaag gggatgtttg agactccaga ggataaaatt tttgccaact tttctaaggt      1260
aaaagcagaa gcagaagcac tttatccaga cttaactatt tattatggag gtgaacttta      1320
ttacacccta gacattgtgg agaaacttga aaagaatctc attccgcgca tgcacaacac      1380
tcaatttgct ttgattgagt ttagtgctcg cacatcttgg aaagaaattc atagtgggct      1440
tagtaatgtt ttgagagcgg gggtaacgcc tattgttgct catattgagc gctatgatgc      1500
cctcgaagaa aatgctgatc gtgttagaga aattatcaat atgggctgct atactcaagt      1560
caatagctca catgtcctca aaccaaagct ctttggagat aaagaaaaag taagaaagaa      1620
acgtgttcgc ttttttcttgg agaaaaattt ggttcatatg gttgctagcg acatgcataa      1680
tcttgggccg agaccaccat ttatgaaaga tgcttatgaa attgttaaaa agaactacgg      1740
ctccaaacgt gctaagaatc ttttttattga aaatcccaaa acattactag aaaatcaata      1800
tttataggag atattatgaa tcaagataac actaaaagtg atgaaatcga cgtactagca      1860 ttgctcacata aactttggac gaagaagctt ttgattcttt tcacagcttt ttatttcgct      1920
gctttcagtt tcttaggtac ttatttcttt atccaaccaa catatacatc aacaacgctt      1980
atctatgttg ttaatcaggc aacagataat aataatcttt ctgctcaaga tttgcaagct      2040
ggtacctatt tggcaaatga ctataaagag attattacat caaatgatgt attatcagaa      2100
gttattaaag atgaaaaatt gaatttgagt gaggcagaac tgtctaaaat ggtttcagtt      2160
aatattccta ctgatactcg tcttatttca atttctgtta atgctaaaac tggtcaagat      2220
gcgcaaacac ttgctaataa ggttcgtgaa gttgcttcaa aaaaaatcaa gaaggtgaca      2280
aaagttgaag atttcacaat gctcgaagaa gctaaattgc cagagtcacc atcttccacca     2340 aatatcaaac ttaatgtgct tcttggggca gtgcttggag gattccttgc agtggttggt      2400
gtattggtac gtgaaatcct agatgatcgt gttcgccgtc cagaagatgt ggaagatgcc      2460
cttggaatgg cacttcttgg aattgtccct gatacagata aaatttaagg agaagaaatg      2520
cctctattaa agttagtaaa atctaaagta aactttgcca aacaaacaga gagtattac       2580 aatgccattc gcacaaatat tcaattttct ggtgctcaga ttaaagtgat tgcgattagc      2640
tctgttgaag ctggtgaagg aaaatcaacg acatctctta acttggcgat tcatttgct       2700
```

-continued

```
agtgttgggc tccgaacact tctgattgat gctgatactc gtaattctgt ttttcaggt    2760 acatttaaat caaatgagcc ttataaaggt ctttcaaatt ttctttcagg aaatgccgat    2820
ctaaatgaaa cgatttgcca aactgatatt tctggtttgg atgttattgc atctggtcct    2880
gttccaccta atccaacaag tcttttgcaa aatgacaatt ttagacattt gatggaagtt    2940
gctcgtagtc gttatgatta tgtcatcatc gatacaccac cagttggttt ggttattgat    3000
gcagttatta ttgcccatca ggctgatgcc agtcttttgg ttacagcagc tgggaaaatc    3060
aaacgtcgtt tcgtaactaa ggccgtcgaa caattggaac aaagtggttc tcagttctta    3120
ggtgtcgtcc ttaataaagt tgacatgaca gttgataaat atggatcata tggttcttac    3180
ggatcatatg gttcttacgg atcatatggt gagtacagga aaaaacaga ccaaactgaa    3240 ggtcattcaa gagcacatcg tcgtagaaaa ggatagcatt aatggggatg atgcggctcc    3300 ttataccta acagattaaa aaggggttta gagtgaaaga aaaacaagaa attcgtcgca    3360
ttgaaattgg tattatacag ttggttgtgg ttgttttcgc agccatggta gctagtaaaa    3420
taccatatac agagattacc caaggaagta ttgtccttt aggtgtcgta catgtagtgt    3480
cttactatat cagtagttat tatgaaaatc ttaagtatag aggctacttg gatgaactca    3540
ttgcaactgt caaatattgt ttcatatttg ctctaattgc aacatttctc tcgttttttg    3600
cagatggaag ttttcaatc tcacgtcgcg gacttcttta cgtcaccatg atttcaggtg    3660
ttctcttata cgttacaaat actgttctta agtatccg ctcatctatt tatacacgtc    3720 gtaaagtaa caagaatatt ctcttgattt ctgatcaggc acgtcttgat aatgttttgt    3780
ctcgtatgaa agacaatatg gatggtagga ttacagcagt ttgtgtcttg ataatccttt    3840
attttactga tccatttatc aagagtgtta aacctgaaaa tttgattgaa tatgcgacac    3900
actcagtagt agaccaagtt ttgattaatc tgccaagtgg gcagtataag atttgggatt    3960
atgcatcacc ttttgagatc atgggaattc cagtttctat taatttgaat gcccttgaat    4020
ttatgagtca aggtgaaaaa cgtattcaac aattgggtcc tttcaaagtt gttacgtttt    4080
caacgcaatt ttatagctat ggagatatct tggcgaaacg tttcctcgat atctgtggag    4140
ccctagttgg tttggtgctc tgtgggattg ttggaatctt cctttatcca cttattcgta    4200
aggatggtgg gccagccatt tttgctcaag accgtgtggg agaaaatgga cgtatcttta    4260
agttttataa attccgttct atgtgtgttg atgcggaaga aatcaagaag atttgatgg    4320 cacagaatca aatgtctggt ggtatgttta agatggacaa tgatccacgt attaccaaaa    4380
ttggacgttt cattcgtaaa acaagtcttg atgaacttcc acaattttgg aatgtcctaa    4440
aaggtgatat gagcttggtt gggacacgtc ctccaacagt tgatgagtat gaaaaatata    4500
cacctgaaca gaaacgtcgt ttaagtttta aacctggtat cactggtctt tggcaagtaa    4560
gcggtcgaag tgaaattact gattttgatg aagttgtaaa actagacgtt gcttatttgg    4620
acggatggac aatctggcgt gatatcaaaa tcttattgaa aacaattaaa gtagtagtaa    4680
tgaaggatgg agcaaagtga tggctttcac catttctttt aatggtgatt aaatgacaaa    4740
aacagtttat atcgttggtt ctaaggggat tccagcaaaa tatggtggat ttgagacctt    4800
tgttgagaag ttgacagagt tccaacaaga caaagatatc caatattatg tagcttgtat    4860
gcgggaaaac tctgcaaaat cagacattac agcagatgat tttcaaactt cgcaacagaa    4920
ccctaaaaag aactccctaa cggtcgtggc tactttgttt agtctaaaca ctttgaatag    4980
tcctacaagc tcatagtttc ccttttatta gttggtccaa ggccaattct atttttgaa    5040 gcgaaagaat atggggagcg ccttccttat ttactgatat gtaaacctgg aattactggt    5100
```

```
tattggacga cacatggtcg aagtaaagtt ctttttcctc aacgagcaga tttagaactc   5160
tattatctcc aatattacag caccaagaac gacatcaagc ttctaatacg tacaatttca   5220
caaatcatta acggattgga cgcttactaa aaaattaatg aaaaaatatt tgaaatcata   5280
actcgaaaaa tattaaaaga ttagatatgt atcataaaac ccgaattgct agttaatttc   5340
attggaaaat aaataagtcg tgctatccta atcttaaacc actaagcatt agaaagcgca   5400
cgacttatat gacttataat agcacacttc caaaagtttt tgtttattta ctgacaacca   5460
ttgagacgct ttatcaaacg agtgttcccc ttgaggttca aaaccgaaag aacgtccatc   5520
tcgcaacatc agattgctta gttatcgctt gttacctatg gggcgtactg cattttagtg   5580
aaacgcttaa agcaaagcac caattggctc aaagtttatt tcctaatttc ctagaatatt   5640
ctcactttgt ccgccgttgt aatgccctct taccgagtat ccaagtcatt cgccaagcac   5700
tcgtatttaa agaggttgaa ggaattagtg tatccattat tgacagcttc cccattcctt   5760
tgtgtcagtc tattcgtaat ttcagaagca aagttcttgg agattatgca aatgttggct   5820
acaatgctac aaagggacag tacttctatg gatgtaaatg tcatgcttta gtcagtgaat   5880
caggctatgt catagactac acaattactc ctgcttcaat ggctgatagt tcaatgaccg   5940
aggaagtgtt gagtcaattt gggacaccaa cagtccttgg agatatggga tatttaggtc   6000
agtcactgca tgataggctg gaattaaaag gaattgatct aattacaccT gtcaggaaga   6060
acatgaagca aaagaaaatt cttttcccta atttttcaaa acgtagaaaa gtgattgagc   6120
gagttttctc ttttttgaca aatctaggag ctgagcgttg taaaagtcgt tcgcctcaag   6180
gttttcaatt gaaattagag atgatacttt tagcgtattc tttactgtta aaatcagcta   6240
aatcactgga accagagact ttaagatatt ctatcgggta tcaagtcatg gctaaataat   6300
caactagcaa ttcgggtatc ataaaggagt gatttaatga aaaaaattac aatagcagtt   6360
gcaacgcata aaaatatca aatgccaaaa gataatattt atctaccaat tgaatgtgga   6420
gcagttttaa gaaaaaatca cctagactat attgctgatg atagtggaga taatatttct   6480
gaaaaaaaca gaattattc agagttaaca gcactatatt ggttatggaa aataatgat   6540 tctgagtata aaggattagc acactataga cgtcattttt cagataaaaa ggtgagtatt   6600
ttttctacag gtaattttga taatatactt gataggacgg tacttgagga acatttagag   6660
aagtttgata ttatacttcc caagcttcga cattactata ttgaaacaat agaatctcac   6720
tataaacata cgcattttga aaaagattta ttagcaacag aagaaataat taaaaaacta   6780
tatcctgact atcttgattt ttattatagt gcactaaaaa gaaaatctgc tcatatgttt   6840
aatatgttta ttatgaaaga taaatatttc aataattatt gtgaatggtt attttcgatt   6900 cttttgaat tagaaaaagt actagatatt tcagaatatt ctcccttcca tgcaagagta   6960
tttggtcgtg tgagtgaaat tttattagat gtatggattt tcaagaataa tttaaatttc   7020
actgaaattc cagttatgtt tatggaaaag caaaattggt gggataaatc taaaagatt   7080 atttctgcaa agcttttcaa caaaaaatat tattagacta ggagaaataa attgcttaca   7140
atcggaataa ttttaataat ttttatgact attttcgatt attatataca taaaacagta   7200
ttttctccgg tctttatgtt taattcactc ttttttattaa taatatctct ttcttctatg   7260
aggttatata atttgagaga atattctatc aaatcaatag aagtaattgt gttagggatg   7320
atattcttct ctttaggagt attttgtact cgtattgttt ctcatgaatt ttaaaaaat   7380 caaaataatg ttattaatta cgatgataat ttaaatgtaa attggacttt tttaaaaatt   7440
cttttgatag ttgtaaccac aggaaacgta ttctctatta ttttttcctt gaaattccctt   7500
```

```
ttaggaggag gttcatactt agaattgaga aatatgatat tgggatataa tggagctgaa    7560
ccacttatta cgaatcctct cgtaaatata ttaacaagat atatatcggg accaggttg     7620 actgctttga tcccatttc tatttttttt ctaattagga aaaaaaacat taaattttcc     7680
ttaattattt tattgaatct tgttttggca acattatcat ccggtggtag aattttactt    7740
gtatatacta ttattcaatt gtttatagga ttatcttatt caaaaaaaaa tataccaaaa    7800
aaaattaaga aagtagtcat aatatcaagt attatatttt ttatatctat aattgtctta    7860
tctaacatca gaagttctaa cagtatatat agagcgtttt atgcatactt ttcgggccct    7920
gtagttcttt tatctacttg gatgactgat gttgatactt ataatattca ttcacatgga    7980
ttaggattta tttatcccat cacatatcta ttaaattcat tttgtaattt aataggaatt    8040
cctaactcga tgttggctaa tgttgtcatg tggcaaggaa tgcctcagaa tgattgggta    8100
ggcgtattcc ctaatcaatc gatgaacgct tttagtacac ttttctattt tttctataaa    8160
gattttcgag aatttggagt tgcttgcttt tctttccttt tgggagtat ttgtggtttt     8220 atttatttta aagcgtttat cgaaagaaaa agtaaatatc tagtctatta tttattaggg    8280
gtacaggcaa ttatcggatc ttttattatt tggcaattgg ggagtactgc gtttttctta    8340
agtattgtat ttcaatatt aagtctgaaa tcaaagaaat cataactata gaaaggaga     8400 taaaatatga caatcagcat agtaatccca gtttataatg ttcaagatta cataaaaaag    8460
tgtctagatt ctatattaag ccagacattt tcagatttag aaattattct tgttgatgat    8520
ggttctactg acttgagtgg aagaatttgt gattattatt ccgaaaatga taaacgtatt    8580
aaagtaatcc acacagcaaa tgggggacag tcggaagcaa ggaacgttgg aatcaaaaat    8640
gccacatcag aatggataac atttattgat tctgatgact acgtttcttc tgattatata    8700
gagtatttat ataatttgat tcaagtacac aatgcagata tttcaatagc tagttttacc    8760
tatatcacac ctaaaaagat aattaagcac ggtaacggtg aagtagctct tatggatgca    8820
aaaactgcaa ttcggagaat gttactgaat gaaggtttcg atatgggagt ttggggaaa    8880 atgtatcgaa cggagtattt taataaatat aaattcgttt caggaaaact atttgaagat    8940
tctttaatta cataccagat atttcagaa gcttcaacaa ttgtttttgg agcaaaggat     9000
atttattttt atgttaacag gaaaaattct actgttaatg gtacttttaa tataaaaaag    9060
tttgatctta ttgaaatgaa tgaagaagca aataagttta ttaaacataa atttccagat    9120
ctttcatctg aagcacatcg tcgaatgata tgggcatatt ttagtacact aaatcaagtt    9180
ttatcatcaa ctaatgaaca cgatattgat ttatatgcgc cacaattagt agcttatctc    9240
cttaaacagg ataaattcat aaaaaggaat acttttattc ccaaaagaga taagattgca    9300
ttttttattt taaaaaattt tggttttaaag acatatcgta atgtttggaa tttatatta    9360 aaaatgacaa gataaaaaca ataatgaaag ataaaaaata atgaaaactg ctacaattac    9420
tttacattca gcacataata atggatctat cttttctaca gtcatttgct ttgcagagaa    9480
agataatatc tatgggatat gataacgaaa ttataaatta tattccactc aaattgctcg    9540
tagttttaag aaccaagtgc aaaagattat taaggttaac aacgttacga ttgttgctac    9600
ggccgcaacg ccgaagaagc cgctgaatac gttgattggg ctagttgtcg gcttgctata    9660
ggatttgttt atgcagcgat tcggatgctc acggatcgcc gcgttcacga agctgatttc    9720
ttaactgatg aattaggatt gactagttta ggcttggtta accatcaaca tcaccattca    9780
atgaagaaac aggccttgaa tctgaacggt ggctatcata cgcataacga tcaaacatct    9840
tcacaagcga tgaaacgagt ttaggagggt gctagatgtt taaacgtaaa gaaaagaata    9900
```

```
taacgactac ggcaccaatt aatctcacca cgattaatga acccatgtcg gtcattactg    9960
agcagattaa aacaattcga accaatatca attttgcggc tactgaccat aagctacgaa   10020 cttttgatggt gacttcggcc atgcttggcg agggtaaatc gacagtaagt ggtaacttag   10080
cagtggagta tgccaaggaa ggaaggcaag caagtcttac tggtcgatgc tgacttgcga   10140
cgaccaacga ttcataagac atttggcctt aaaaaccata agggattaag ttcatggtta   10200
gccaatcaga ttgacgatgt gaatgatgca attcatcccg tcattggcaa tctataattg   10260
tataaatagt atgtatactt tataacaatg gagtgtttta atgaatcttt tgtttagtca   10320
atgtcacatt acattgaaaa tttaaaaaat gtaactttt tgcgtgtgaa tagctatgta    10380
caatgatttt ctgggtggca gactaatcaa gtataaaata gcttatacta gttgacaaca   10440
tcccgtgata attattaact tatcaagtac aggccaaaat actggagctt aacaggaact   10500
gttagaatat gatttatat aattaggagt agaataaaga gatgaatcca ttaatatcaa    10560
ttattgttcc aacatataat gttgaaaaat atattaggac atgtattgaa tcaatcttag   10620
ctcaaacata tcgcaatatt gaagtcatta tagtaaatga tggtagcaca gatcagtcgc   10680
tagcagtaat ttccgattta atctgtagtc atcataatat taaggtaatc aaccaaaaaa   10740
accaaggatt atcagtagct cgaaacactg gtattgatgc ggcaactggt aaatatatag   10800
cttttgtaga tgcagatgac aaaattaagc cagactttgt tagctcgctc tatcaaattg   10860
ctgacaaaac aggagctgac attgtgcgtg ggtcatttcg agactttaat ggcaatattc   10920
ctaaaggctg ggttccagat ttcaatgttc caaccaatta tgggacaata gtattagacc   10980
aattcttatc cagcaacata tcttttgtag tttggtcgag tatctatagg ctagattta    11040 ttaatagtaa tcatatacga tttacaccag ggattctatt tgaggatgca gattttacaa   11100
taagagctta tgctcgcta aagtagttg ctacatcacc tgaaccaaat tatgcatata     11160
gaataaatcg tccaggaagt atattaacca caaaaccac aaaaaatgcc caaaaaatgt    11220
ctctttcaga agaaaaaatt atatcacaat ttattagtat gttaaagcat gaaaaatctg   11280
atgttttatg tagtttaatt ctaaagtcta tttatgcatg tatgagagat tggacgggaa   11340
ttattgtgag gaataaccta tcgttggata ggaagaacag ttgttttgat actgctctca   11400
ctctaataaa agaaataata aattctaggc ccttaaaaga aaaaatcaaa ttttttaacaa   11460 aggttattat tattaaggcg aaaaaaccatt aagccgttaa acgaaaatcc aaagggttca   11520
tatacaatta tgttaattat ggattttta tatcttcaat gggttcatta atcactgaat    11580
ttgattatct tgttttaatg aatgtgaagt cattcggtta aggggagtct ttgatttgtc   11640
tagttagcta tctggacaga tgttaagtgt taattacagt gaaggcagat gaaaacttat   11700
taaaagttat tctgcttgat taagaatggt aagatttcac catctatata cttttattag   11760
aacttaggtg gacaggagga cccaattttt aatccttcct gttatatagt ttttgtttaa   11820
tatttttcgg gaggattatt aatgcaaata gtaaaaaaatt atctttataa tgcaatgtat   11880 caggtctta taattattgt gccattactt accattcctt atttgtcaag aattttgggc    11940
ccttcaggta ttggaattaa ctcatatacc aattctattg ttcagtattt tgttttattt   12000
ggtagtatag gagtcggttt gtatgggaat cgtcagattg cctttgttag ggataatcag   12060
gtcaaaatgt ctaaagtctt ttatgaaata tttattttaa gactattaac aatatgttta   12120
gcatatttat tgttcgttgc tttttttaacc attaatggtc agtatcatga atactatttg   12180
tttcaatcca ttgctatagt tgcagctgca tttgatatct cttggttttt tatgggaatt   12240
gaaaatttta aagtaactgt attaagaaat tttatagttc agttacttgc tctattcagt   12300
```

```
attttcctat tgtcaaatc ttacaatgat ttgaatatat atatattgat aacagttttta    12360
tctacattaa ttggtaattt aacttttttc ccaagtttac acagatatct cgtaaaggtt    12420
aactatcgtg aattaaggcc aataaagcat ttaaagcaat ctttagttat gtttatccca    12480
caaattgctg tccaaattta ttgggttttg aataaaacaa tgttaggttc attggattct    12540
gtcacgagct ccggctttttt tgatcagtct gataaaatag ttaaactggt tttggctatt    12600
gctagtgcaa caggtactgt catgttgcca cgtgttgcaa atgcctttgc acatagagag    12660
tatagtaaaa ttaaggagta catgtacgca ggttttttctt ttgtgtcggc aatttcgatt    12720
cctatgatgt ttggtctgat agctattact cctaaattcg tgccactttt ttttacatct    12780
caatttagtg atgttattcc tgtgttaatg atcgagtcaa ttgcaattat ttttatagct    12840
tggagcaacg caataggtaa tcaatatctt ttaccaacta atcaaaataa gtcatataca    12900
gtgtcggtgt tcattggagc gatagtcaat ttaatgttaa atattccact gattatatat    12960
ctaggtgctg ttggtgcatc aattgcaact gtaattctg aaatgtctgt aactgtgtat    13020
caactttttta taattcataa acagcttaat ttgcatacac tgttttcgga tttatctaag    13080
tatttaattg caggattagt gatgtttcta attgtcttta aaattagttt gttaacaccg    13140
acatcttgga tattcattct gttggaaatt actgtgggca taattattta tgttgtttta    13200
ttaatatttt taaaggcaga aataattaat aaactaaagt ttattatgca taaatagagg    13260
tatgatttta ggtacctgcc tttaggatt ttaattcaaa ggatttaggt acttatggtt    13320
actttaattc gattgtgacc tactttattc ttttggcaac tttaggtgtt gctaactatg    13380
gtactaaaga gatttcagga catcgaaagg atattcgtaa aaatttctgg ggtatttata    13440
ccctccaatt gattgcgact attttgtctc ttgtcttgta tacatcatta tgtttgttct    13500
ttcctggtat gcaaaatatg gtggcttata tcttaggatt aagcttgata tcgaaaggaa    13560
tggatatttc ttggttattc caaggtttgg aggattttcg tcgtattacc gcaaggaata    13620
caacggtaaa ggttttagga gttatttcta tcttcctatt tgtgaaaaca cctggtgatt    13680
tgtatctcta tgttttccta ttgaccttct tgaattgct tgggcaatta agtatatggt    13740
taccagcgag accttacatt ggaaaaccac aatttgattt atcctatgct aagaaacatc    13800
ttaaacctgt tattttgctg tttctcccctc aggttgccat tcactatac gtgactttgg    13860
atcgtacaat gttgggtgcc ttgtcatcga caaatgatgt agggatttat gatcaggctt    13920
tgaaaataat taatattttg ttgacgttgg tgacttcatt gggaagtgta atgcttccaa    13980
gggtatctgg tcttttatct aacggagatc ataaggccgt taacaagatg catgaattct    14040
ctttcttgat ttataatctt gtgattttcc cgataatagc aggtctcttg attgttaata    14100
aggattttgt gagtttctta ctagggaaag atttccaaga ggcttatctt gccattgcta    14160
ttatggtctt taggatgttc tttatcggtt ggacaaatat tatgggaatc cagatttga    14220
ttccatataa taaacatcgt gagttcatgc tctctacgac tattccggct gttgtcagtg    14280
ttggacttaa tctcttgtta atttcctcca tttggctttg ttggggtctc aattgtatca    14340
gttttaacag aggctttggt atgggttatt caattgaatt tttcaaggat attcatcaaa    14400
gatgtgtcaa tccttccagc catatcaaaa attatcttag catcagttgt catgtatctt    14460
ggactcttttg tctttaagat gtttgtgcaa ttgaaaccaa tgctaaatgt agcagtagat    14520
ggtcttgtcg gtgctatcat ttatattgtc ttgattattg tcttacgtgt cgttgatatg    14580
aaagacttga agcaacagtt aatgaaaaac taaggagaaa aatatgtacg attatcttat    14640
cgttggtgct ggtttgtccg gagcaatctt cgcacatgaa gctacaaaac gtggcaaaaa    14700
```

```
agtaaaagtg attgacaagc gtgatcacat tggtggcaat atctactgtg aagatgttga    14760
aggtattaat gttcacaagt atggtgctca cattttccat acctcaaata aaaaagtttg    14820
ggattatgtc aaccaatttg ctgaatttaa taactatatc aactcaccaa ttgctaacta    14880
caagggcagt ctttataacc ttccatttaa catgaataca ttttatgcta tgtggggcac    14940
taagactcct caagaagtta aggacaagat tgctgaacaa acggctgata tgaaagatgt    15000
tgagcctaaa aacttggaag aacaagctat caagttgatt ggaccagata tctacgaaaa    15060
gttgatcaag ggatacactg aaaaacaatg gggacgttct gccacagacc tgcctccttt    15120
catcatcaag cgtcttccgg ttcgtctaac ttttgataac aactacttta atgaccgtta    15180
ccaaggaatt ccgatcggtg gttacaatgt catcattgaa aatatgcttg gagatgtaga    15240
agtagagctt ggagttgact tctttgccaa tcgtgaagag cttgaagctt cagctgaaaa    15300
agttgtcttt acaggaatga ttgaccagta ctttgattat aaacatggtg agttggagta    15360
tcgcagtctt cgttttgaac acgaagtctt ggatgaagaa aatcatcaag gaaatgccgt    15420
ggtcaactac acagagcgtg agattcctta tactcgtatc attgagcata agcacttcga    15480
gtatggtaca caacctaaga cagttatcac acgtgaatac ccagctgatt ggaaacgtgg    15540
agatgaacca tactacccaa tcaatgatga aaagaacaat gccatgtttg ctaagtacca    15600
agaagaagct gagaaaaatg acaaggttat cttctgtgga cgtcttgcag attataaata    15660
ctacgacatg cacgtggtca ttgagcgtgc tctagaagtc gttgagaaag aatttattta    15720
ataaataatg gctctttgtc aactgtagtg ggtgacgaaa agctaacatc tagagaggac    15780
cggataggtc ctcttttat gtatgttcag tgtgatgaag acacgtttct aaagttgat    15840 gaagtttcta aaaccgaagc ccaaccgttt gatgtctttg atcaacttat tagtcgcttc    15900
aagttttgcg tttggatagt ccgtttctag tgcgttttg atgtattgct tgtgtctaag    15960
aaaagtccta aagacagttt gaaatagtg attgaccttg ctcctatttt cctctatcag    16020
gtcaaagaac tcatctactc tcttctcctg aaagtgaaaa agcaaaagct gataaagtgt    16080
atagtagtca gtaagctctt ttgaaaagac tagtgtcttc gcaacaactt catgtggtgc    16140
taaagtttgg cggaaagtct ttgaataaaa agaattgaga gatagtttac agctgtcctt    16200
ttggaagagt cgccagtgat ttttcaaggc tcgatagggt agtgacttct tatcgaatta    16260
gttcatgatt gcaattctag tcttaaaaa tgctctacca aggtgctgga tgatgtggaa    16320
acgatcaaga acgattttg cgtttggaaa gagtctgcgg gctagtggga tataagctcc    16380
agacttatcc atcgtgataa actgtacctg ttatcggact ttcaatggat acttcaaaag    16440
tagtttcgta tagtagtttg gcggcgatta tcaaggatgg ttatgagttg gtttgtctca    16500
taattctgcg ccacaaaagc caattcccct ttcttgaacc caaactcatc ccaggacata    16560
acagcaggga gtttgtcata atgtttcttg aaagtaaact gatcaagctt acgatagaca    16620
gtggacgtcg acacacgaag tcttcttgca atatcagtta gtgacacttt ctcagttagg    16680
agttgtgtaa cttttgttg gactagattg gagatttggt agttttctc aacgatagat    16740 gtctcagcta ccgtgactct cctacaattt ttacactgga aacgacgttt tttcagacgt    16800
agtagagttg gcgttcccgc ttgctcgaga agagggattt tagatttttt ttgaaagtca    16860
tatttgatca tctttctttg gcagtgagga catgatggtg tagggtaatc aagttttgct    16920
tgaatctcga tatgagtgtc agtttcaaaa acaagtgaaa taatgatatt ttggtcttta    16980
actccgatta attctgtggt attcttaata ggtctcataa gttcttccta atggtagttt    17040
cgtcgctttt cattatagtt cttatgggac ttttttgtgta cactcaaaaa gctctataat    17100
```

-continued

```
ctctacagtg gttttactca ctacagaaat tatagagcca atatatctcc tgtctatttt    17160
tatgctactt ttgggttagc tcaactcaac cgccttttaa tctcccaaca acaataatac    17220
cctatcaaac aacccaaaaa attcaagata atatcactaa tggcaaatgt gcccaaataa    17280
aagataaatt gaatggtttc aattcctaaa agtgtgacca aactgataat gacaaactgt    17340
ttgaaattag tattgataca gtaaaggcca cctaaaggaa tgaagta                  17387
```

<210> SEQ ID NO 21
<211> LENGTH: 63
<212> TYPE: DNA
<213> ORGANISM: Streptococcus thermophilus

<400> SEQUENCE: 21

```
caaggacagt tattgatttt ataatcacta tgtgggtata aaaacgtcaa aatttcattt    60
gag                                                                  63
```

<210> SEQ ID NO 22
<211> LENGTH: 41
<212> TYPE: DNA
<213> ORGANISM: Streptococcus thermophilus

<400> SEQUENCE: 22

```
ttgattcaac ataaaaagcc agttcaattg aacttggctt t                        41
```

<210> SEQ ID NO 23
<211> LENGTH: 24
<212> TYPE: DNA
<213> ORGANISM: Artificial
<220> FEATURE:
<223> OTHER INFORMATION: Oligonucleotide primer

<400> SEQUENCE: 23

```
aaatgaattc agagcaagca cttg                                           24
```

<210> SEQ ID NO 24
<211> LENGTH: 24
<212> TYPE: DNA
<213> ORGANISM: Artificial
<220> FEATURE:
<223> OTHER INFORMATION: Oligonucleotide primer

<400> SEQUENCE: 24

```
gtcatgtcaa ctttattaag gacg                                           24
```

STREPTOCOCCUS THERMOPHILUS LACTIC ACID BACTERIUM

This application is a continuation of U.S. application Ser. No. 12/304,913, filed Dec. 15, 2008, which claims priority under 35 USC 371 to International Application No. PCT/IB2007/002639, filed on Jun. 8, 2007, which claims priority to U.S. Provisional Application Ser. No. 60/804,978, filed Jun. 16, 2006, each of which is incorporated by reference in its entirety.

FIELD OF INVENTION

The present invention relates to inter alia a fast acidifying lactic acid bacterium with improved texturizing properties.

BACKGROUND TO THE INVENTION

The food industry uses bacteria in order to improve the taste and the texture of foods and also to extend the shelf life of these foods. In the case of the dairy industry, lactic bacteria are commonly used in order to, for example, bring about the acidification of milk (by fermentation) and to texturize the product into which they are incorporated. Among the lactic bacteria commonly used in the food industry, examples include the genera *Streptococcus, Lactococcus, Lactobacillus, Leuconostoc, Pediococcus* and *Bifidobacterium*.

The lactic acid bacteria of the species *Streptococcus thermophilus* are used extensively alone or in combination with other bacteria for the production of food products, in particular fermented products. They are used in particular in the formulation of the ferments used for the production of fermented milks, for example yogurts. Certain bacteria play a dominant role in the development of the texture of the fermented product. This characteristic is closely linked to the production of polysaccharides. Among the strains of *Streptococcus thermophilus* it is possible to distinguish texturizing and non-texturizing strains.

In addition, cultures—such as starter cultures—are used extensively in the food industry in the manufacture of fermented products including milk products (such as yoghurt, butter and cheese), meat products, bakery products, wine and vegetable products. The preparation of cultures is labour intensive, occupying much space and equipment, and there is a considerable risk of contamination with spoilage bacteria and/or phages during the step of propagation. The failure of bacterial cultures by bacteriophage (phage) infection and multiplication is a major problem with the industrial use of bacterial cultures. There are many different types of phages with varying mechanisms to attack bacteria. Moreover, new strains of bacteriophages appear.

Strategies used in industry to minimise bacteriophage infection, and thus failure of a bacterial culture, include the use of: (i) mixed starter cultures; and (ii) the alternate use of strains having different phage susceptibility profiles (strain rotation).

(i) Traditionally, starter cultures in the dairy industry are mixtures of lactic acid bacterial strains. The complex composition of mixed starter cultures ensures that a certain level of resistance to phage attack is present. However, repeated sub-culturing of mixed strain cultures leads to unpredictable changes in the distribution of individual strains and eventually undesired strain dominance. This in turn may lead to increased susceptibility to phage attack and risk of fermentation failures.

(ii) The rotation of selected bacterial strains which are sensitive to different phages is another approach to limit phage development. However, it is difficult and cumbersome to identify and select a sufficient number of strains having different phage type profiles to provide an efficient and reliable rotation program. In addition, the continuous use of strains requires careful monitoring for new infectious phages and the need to quickly substitute a strain which is infected by the new bacteriophage by a resistant strain. In manufacturing plants where large quantities of bulk starter cultures are made ahead of time, such a quick response is usually not possible.

There is a continuing need in the art to provide improved bacterial strains for use in the food/feed industry—such as bacterial strains that have improved texturizing properties. Improved bacterial strains that are phage resistant are particularly desirable.

SUMMARY OF THE PRESENT INVENTION

The fast acidifying lactic acid bacterium described herein has numerous advantages. By way of example, the fast acidifying lactic acid bacterium has advantages in terms of texturizing the media into which it is incorporated. By way of further example, it makes it possible to obtain gels from, for example, fermented milks, which are thick, sticky, coated, stringy, resistant to stirring and/or not granular.

Advantageously, the fast acidifying lactic acid bacterium is bacteriophage resistant thereby minimising bacteriophage infection, and thus failure of the bacterial culture. This is an important property of the lactic acid bacterium described herein because it reduces the risk of phage incidents during production, which may stop production for a period of time for decontamination.

Most advantageously, the fast acidifying lactic acid bacterium described herein has advantageous texturizing properties and is also phage resistant.

SUMMARY ASPECTS OF THE PRESENT INVENTION

Aspects of the present invention are presented in the accompanying claims.

In a first aspect, there is provided a fast acidifying lactic acid bacterium that generates a viscosity in fermented milk greater than about 62 Pa·s.

In a particularly preferred aspect, there is provided a fast acidifying lactic acid bacterium that generates a viscosity in fermented milk greater than about 62 Pa·s and which bacterium is phage resistant.

In another aspect, there is provided a lactic acid bacterium comprising the sequence set forth in SEQ ID No. 19 or a homologue thereof with at least 75% identity thereto.

In a further aspect, there is provided an isolated *Streptococcus thermophilus* strain deposited under the Budapest Treaty by Danisco Deutschland Niebüll GrnbH, Buch-Johannsen Strasse.1, Niebüll-D-25899, Germany at DSMZ (Deutsche Sammlung von Mikroorganismen and Zellkulturen GmbH, Mascheroder Weg 1 b, D-38124 Braunschweig) under deposit number 18344 on 14 Jun. 2006. We hereby confirm that the depositor has authorised the applicant to refer to the deposited biological material in this application and has given his unreserved and irrevocable consent to the deposited material being made available to the public.

There is also provided a cell culture comprising the lactic acid bacterium or the strain described herein.

In a further aspect, there is provided a food, food additive, feed, nutritional supplement, or probiotic supplement comprising the lactic acid bacterium, the strain, or the cell culture as described herein.

A method for preparing a food, food additive, feed, nutritional supplement, or probiotic supplement comprising the step of adding the lactic acid bacterium, the strain, or the cell culture to said food, food additive, feed, nutritional supplement, or probiotic supplement.

In a further aspect, a food, food additive, feed, nutritional supplement, or probiotic supplement obtained or obtainable by the method described herein.

There is also described the use of the lactic acid bacterium, the strain, or the cell culture for preparing a food, food additive, feed, nutritional supplement, or probiotic supplement.

In a further aspect, we described a method for modifying the viscosity of a food, food additive, feed, nutritional supplement, or probiotic supplement, comprising adding the lactic acid bacterium, the strain, or the cell culture to said, food, food additive, feed, nutritional supplement, or probiotic supplement.

A food, food additive, feed, nutritional supplement, or probiotic supplement obtained or obtainable by the method is also provided.

There is provided, in a further aspect, the use of the lactic acid bacterium, the strain, or the cell culture for modifying the viscosity of a food, food additive, feed, nutritional supplement, or probiotic supplement.

A method is also described for identifying a bacterium belonging to the genus *Streptococcus* comprising the step of screening the bacterium for the sequence set forth in SEQ ID No. 19 or a homologue thereof with at least 75% identity thereto.

A method for identifying a bacterium belonging to the genus *Streptococcus* is also described comprising the step of amplifying the CRISPR locus of a bacterium using at least one forward and at least one reverse oligonucleotide primer, wherein each of the primers flank opposite sides of one or more CRISPR spacers that are absent in *Streptococcus thermophilus* DSMZ-18344.

A bacterium belonging to the genus *Streptococcus* that is identified or identifiable by the method is also provided in a further aspect.

In another aspect, there is described a nucleotide sequence comprising the sequence set forth in SEQ ID No. 19 or a homologue thereof with at least 75% identity thereto.

A nucleotide sequence complementary to the nucleotide sequence is also provided, as is a construct or a vector comprising the nucleotide sequence In a further aspect, there is described a host cell comprising the construct or the vector.

An oligonucleotide primer that is capable of hybridising to the nucleotide sequence is also provided.

In still a further aspect, the use of the oligonucleotide primer for identifying a bacterium belonging to the genus *Streptococcus* is described.

There is also provided a lactic acid bacterium, an isolated culture, a cell culture, a food, food additive, feed, nutritional supplement, probiotic supplement, a method, a use, a nucleic acid sequence, a construct, a vector, a host cell, an amino acid sequence, or an oligonucleotide primer as hereinbefore described with reference to the accompanying description and figures.

Other aspects of the present invention are presented in the accompanying claims and in the following description and discussion. These aspects are presented under separate section headings. However, it is to be understood that the teachings under each section heading are not necessarily limited to that particular section heading.

PREFERRED EMBODIMENTS

Preferably, the bacterium is phage resistant.

Preferably, the bacterium is selected from the group consisting of *Streptococcus, Lactococcus, Lactobacillus, Leuconostoc, Pediococcus* and *Bifidobacterium*.

Preferably, the bacterium is *Streptococcus thermophilus*.

Preferably, the *Streptococcus thermophilus* belongs to the genetic cluster CL0189.

Preferably, the lactic acid bacterium comprises the sequence set forth in SEQ ID No. 20.

Preferably, the cell culture is a starter culture, a probiotic culture or a dietary supplement.

Preferably, the culture comprises one or more further lactic acid bacteria selected from the genera consisting of *Streptococcus, Lactococcus, Lactobacillus, Leuconostoc, Pediococcus* and *Bifidobacterium*.

Preferably, the culture comprises one or more further lactic acid bacteria selected from the species consisting of *Lactobacillus delbrueckii* subsp. *bulgaricus, Lactobacillus acidophilus, Lactobacillus casei* and/or *Bifidobacterium*.

Preferably, the food, food additive, feed, nutritional supplement, or probiotic supplement is a dairy, meat or cereal food, food additive, feed, nutritional supplement, or probiotic supplement Preferably, the dairy food, food additive, feed, nutritional supplement, or probiotic supplement is a fermented milk, yoghurt, cream, matured cream, cheese, fromage frais, a milk beverage, a processed cheese, a cream dessert, a cottage cheese or infant milk.

Preferably, the milk comprises milk of animal and/or plant origin.

Preferably, the food, food additive, feed, nutritional supplement, or probiotic supplement comprises or consists of a fermented food, food additive, feed, nutritional supplement, or probiotic supplement.

Preferably, the food, food additive, feed, nutritional supplement, or probiotic supplement comprises or consists of a dairy food, food additive, feed, nutritional supplement, or probiotic supplement.

Preferably, the forward oligonucleotide primer hybridises to SEQ ID No. 1 and the reverse oligonucleotide primer hybridises to any of SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16 and/or SEQ ID No. 17.

Preferably, the forward oligonucleotide primer hybridises to any of SEQ ID No. 2, SEQ ID No. 3, SEQ ID No. 4, SEQ ID No. 5, SEQ ID No. 6, SEQ ID No. 7 and/or SEQ ID No. 8 and a reverse oligonucleotide primer hybridises to any of SEQ ID No. 9, SEQ ID No. 10, SEQ ID No. 11, SEQ ID No. 12, SEQ ID No. 13, SEQ ID No. 14, SEQ ID No. 15, SEQ ID No. 16 and/or SEQ ID No. 17.

Preferably, the forward oligonucleotide primer hybridises to any of SEQ ID No. 2, SEQ ID No. 3, SEQ ID No. 4, SEQ ID No. 5, SEQ ID No. 6, SEQ ID No. 7 and/or SEQ ID No. 8 and the reverse oligonucleotide primer hybridises to SEQ ID No. 18.

Preferably, the forward oligonucleotide primer hybridises to any of SEQ ID No. 9, SEQ ID No. 10, SEQ ID No. 11, SEQ ID No. 12, SEQ ID No. 13, SEQ ID No. 14, SEQ ID No. 15, SEQ ID No. 16 and/or SEQ ID No. 17 and the reverse oligonucleotide primer hybridises to SEQ ID No. 18.

Preferably, the bacterium belonging to the genus *Streptococcus* is *Streptococcus thermophilus*.

Preferably, the *Streptococcus thermophilus* strain belongs to the genetic cluster CL0189.

Preferably, the *Streptococcus thermophilus* strain has substantially the same characteristics as the *Streptococcus thermophilus* strain deposited at DSMZ (Deutsche Sammlung von Mikroorganismen und Zellkulturen GmbH, Mascheroder Weg 1 b, D-38124 Braunschweig) under deposit number 18344 on 14 Jun. 2006.

Preferably, the *Streptococcus thermophilus* strain is the same as the *Streptococcus thermophilus* strain deposited DSMZ (Deutsche Sammlung von Mikroorganismen und Zellkulturen GmbH, Mascheroder Weg 1 b, D-38124 Braunschweig) under deposit number 18344 on 14 Jun. 2006.

The term "fast acidifying strain" as used herein preferably means a strain that has the following properties: a speed of acidification of less than −0.0100 upH/min and a time to reach pH 4.6 of less than 540 minutes at 43° C. when the inoculation rate is between 1E6 cfu/ml and 1E7 cfu/ml of milk (following the fermentated milk process described in the section entitled "Fermented Milk Process" below).

Figure 1:
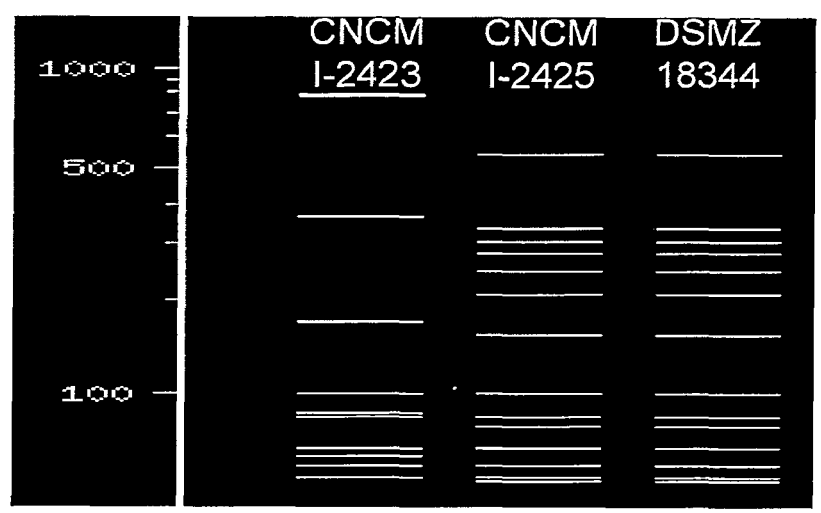
FIG. 1

Comparison of the results obtained using EPSAD PCR-RFLP for *S. thermophilus* CNCM I-2423, *S. thermophilus* CNCM I-2425 and *S. thermophilus* DSMZ-18344.

FIG. 2

Organisation of *S. thermophilus* eps gene clusters. All known eps operons consist of a common proximal part (epsA-B-C-D genes) which is followed by a highly variable part.

FIG. 3

Schematic representation of the sequence of the spacers of the CRISPR 1 locus of *S. thermophilus* DSMZ-18344, *S. thermophilus* CNCM I-2425, *S. thermophilus* CNRZ385 and *S. thermophilus* CNCM I-2423. Each square represents one spacer sequence.

DETAILED DESCRIPTION OF THE INVENTION

Lactic Acid Bacteria

As used herein the term "lactic acid bacteria" refers to Gram positive, microaerophillic or anaerobic bacteria which ferment sugar with the production of acids including lactic acid as the predominantly produced acid, acetic acid, formic acid and propionic acid. They belong to the taxonomic group of the Firmicutes. Devoid of catalase, the lactic bacteria constitute a heterogeneous group of bacteria in the form of cocci for the genera *Aeroccus, Enterococcus, Lactococcus, Leuconostoc, Oenococcus, Pediococcus, Streptococcus, Tetragenococcus, Vagococcus* and *Weissella*, or in the form of rods for the genera *Lactobacillus* and *Carnobacterium*.

The industrially most useful lactic acid bacteria are found among the genera *Lactococcus, Lactobacillus, Bifidobacterium, Streptococcus, Leuconostoc, Pediococcus* and *Propionibacterium*. In one embodiment, it is therefore preferred that the lactic acid bacterium is selected from this group of genera.

In a particularly preferred embodiment, the lactic acid bacterium belongs to the genus *Streptococcus*.

A preferred species of lactic bacterium is *Streptococcus thermophilus*. Preferably, the *Streptococcus thermophilus* belongs to the genetic cluster CL0189.

*Streptococcus thermophilus* is a species naturally present in milk and widely used in the food, and in particular dairy industry because it can be used to acidify and texturise products—such as milk. It is a homofermentative thermophilic bacterium.

As described in further detail herein, lactic acid bacteria starter cultures are commonly used in the food industry as mixed strain cultures comprising one or more species. Mixtures of preferred strains include mixtures of the lactic acid bacterium described herein with one or more *Streptococcus* strains—such as different *Streptococcus thermophilus* strains—or with one or more strains belonging to the genera *Lactococcus, Lactobacillus, Bifidobacterium, Streptococcus, Leuconostoc, Pediococcus* and/or *Propionibacterium*.

Mixtures of the lactic acid bacterium described herein with *Lactobacillus delbrueckii* subsp. *Bulgaricus, Lactobacillus acidophilus, Lactobacillus casei, Lactococcus lactis* and/or *Bifidobacterium* are preferred.

Mixtures of the lactic acid bacterium described herein with *Lactobacillus delbrueckii* subsp. *bulgaricus* are particularly preferred. Such mixed strain cultures are typically used as yoghurt starter cultures where a symbiotic relationship exists between the species (Rajagopal et al. *J. Dairy Sci.*, 73, p. 894-899, 1990).

The lactic acid bacteria and mixtures thereof may be used in the cultures described herein.

In one aspect, there is provided a fast acidifying lactic acid bacterium that generates a viscosity in fermented milk greater than about 62 Pa·s.

In addition an increase in the rate of acidification also reduces the risk of fermentation failure due to phage infection.

Preferably, said bacterium comprises the sequence set forth in SEQ ID No. 19 or a homologue thereof with at least 75% identity thereto.

Preferably, said bacterium comprises the sequence set forth in SEQ ID No. 20 or a variant, fragment, homologue or derivative thereof.

In a further aspect, there is provided a lactic acid bacterium comprising the sequence set forth in SEQ ID No. 19 or a homologue thereof with at least 75% identity thereto.

In a further aspect, there is provided a lactic acid bacterium comprising the sequence set forth in SEQ ID No. 20 or a variant, fragment, homologue or derivative thereof.

In a particularly preferred aspect, the present invention relates to a strain of *Streptococcus thermophilus* deposited at DSMZ (Deutsche Sammlung von Mikroorganismen and Zellkulturen GmbH, Mascheroder Weg 1 b, D-38124 Braunschweig) under deposit number 18344 on 14 Jun. 2006.

The lactic acid bacterium may be a mutant and/or a variant of the lactic acid bacterium described herein. Preferably, this mutant and/or variant lactic acid bacterium has one or more (preferably, all) of the characteristics of the *S. thermophilus* strain of the present invention e.g. the mutant and/or variant lactic acid bacterium is a fast acidifying lactic acid bacterium; and/or the mutant and/or variant lactic acid bacterium generates a viscosity in fermented milk greater than about 62 Pa·s, preferably about 68 Pa·s; and/or the mutant and/or variant lactic acid bacterium is phage resistant; and/or the mutant and/or variant lactic acid bacterium belongs to the genetic cluster CL0189; and/or the mutant and/or variant lactic acid bacterium comprises the sequence set forth in SEQ ID No. 20; and/or the mutant and/or variant lactic acid bacterium comprises the sequence set forth in SEQ ID No. 19 or a variant, fragment, homologue or derivative thereof.

Acidifying Activity

Acidifying activity is typically characterised by three parameters: the kinetics of acidification, the titratable acidity and the final fermentation pH which determines the organoleptic characteristics of the product and its preservation quality, and the post-acidification which develops during preservation of the product.

Advantageously, a high rate of acidification makes it possible to reduce the period during which a product is sensitive to contaminants (pH>4.7) and thereby to reduce the risk of bacterial contamination. An increase in the rate of acidification also enhances the economics of the process by increasing the productivity and the flexibility of the industrial material.

The acidifying activity of lactic acid bacteria may be determined using various methods that are known in the art. By way of example, the lactic acid bacteria may be initially grown in broth and then in sterile reconstituted skimmed milk supplemented with yeast extract and glucose for two successive subcultures. Sterile reconstituted skimmed milk is then inoculated with a 24-h activated culture and pH changes determined using pH meters during incubation.

Advantageously, the lactic acid bacterium according to the present invention is fast acidifying since it can be characterised by a fast acidification of milk during the fermentation process.

Preferably, the speed of acidification is from about −0.013 upH/min to about −0.019 upH/min. More preferably, the speed of acidification is from about −0.0135 upH/min to about −0.018 upH/min. More preferably, the speed of acidification is from about −0.014 upH/min to about −0.017 upH/min. More preferably, the speed of acidification is from about −0.0145 upH/min to about −0.017 upH/min. More preferably, the speed of acidification is from about −0.015 upH/min to about −0.017 upH/min. More preferably, the speed of acidification is from about −0.015 upH/min to about −0.017 upH/min. Most preferably the speed of acidification is about −0.0169 upH/min.

This rate of acidification compares favourably to other fast acidifying strains of bacteria—such as 0.0129 upH/min, 0.0167 upH/min and 0.0209 upH/min for *S. thermophilus* CNCM I-2423, *S. thermophilus* CNCM I-2980 and *S. thermophilus* CNCM I-2425, respectively.

*S. thermophilus* CNCM I-2423 has been previously deposited at the CNCM as deposit number I-2423 and is described in WO2004/085607.

*S. thermophilus* CNCM I-2425 has been previously deposited at the CNCM as deposit number I-2425

*S. thermophilus* CNCM I-2980 has been previously deposited at the CNCM as deposit number I-2980 and is described in WO2004/085607.

Fast acidifying *S. thermophilus* is a bacterium that is typically able to coagulate milk in less than 540 min at 43° C.+/−1° C. when the inoculation rate is between 1E6 cfu/ml and 1E7 cfu/ml of milk. The maximum speed of acidification is the maximum value of the derived curve pH versus time. This final measurement may be obtained using on line pH measurement in milk using a CINAC device (Ysebaert Ltd).

In one embodiment, the rate of acidification is measured using methods that are commonly known in the art. Typically, the rate of acidification will be measured by monitoring the change in pH over time.

In another embodiment, the rate of acidification is measured using a CINAC device which is an extensively used apparatus in the dairy industry to analyse acidification properties of lactic acid bacteria.

An automated system for measuring the rate of acidification is well known to the person of ordinary skill in the art. Reference can be found in (for example) FR 2 629 612 for example. The CINAC automated system is taught in the article Corrieu, G. et al Process (ISSN 0998-6650); 1992, No. 1068, pp 24-27 (10 ref.).

Texturizing/Viscosity

As described herein, a lactic acid bacterium with improved texturizing properties or activities is provided. In particular, the lactic acid bacterium exhibits the property of conferring viscosity to a fermentation medium.

The lactic acid bacterium generates fermented milk having a viscosity greater than about 62 Pa·s, more preferably greater than about 65 Pa·s, more preferably greater than about 68 Pa·s.

Preferably, the lactic acid bacterium generates fermented milk having a viscosity in the range of about 62 Pa·s to about 75 Pa·s, preferably from about 65 Pa·s to about 75 Pa·s, more preferably from about 62 Pa·s to about 68 Pa·s, most preferably from about 65 to about 68 Pa·s, more preferably about 68 Pa·s.

Preferably, the viscosity is measured after 14 days of storage at about 6° C.

The lactic acid bacteria described herein are strongly texturizing.

In one embodiment, the lactic acid bacterium generates fermented milk having the viscosity described herein as measured using the one or more of the methods described below.

Various rheological measurements are known in the art—such as flow and viscosity.

Fermented Milk Process

In one embodiment, fresh fermented milks are produced at lab scale. The milk base is composed of commercial UHT milk supplemented with 3% (w/w) semi-skimmed milk powder. After mixing, the milk base is heated during 10 min+/−1 min at 90° C.+/−0.2° C. The base is then cooled down at 43° C.+/−1° C. in a water bath regulated at 43° C.+/−1° C. and the milk is dispatched into 125 ml glass beakers. The milk is inoculated with the bacterium at a ratio of 1E6-1E7 cfu/ml. The fermentation is carried out at 43° C.+/−1° C. without stirring and it is stopped when the pH reaches 4.6+/−0.05. At this moment, the fresh fermented milk is quickly cooled down at 6° C.+/−1° C. in less than 1 hour. Finally, the products are stored at this temperature during 28 days.

Method to Measure Viscosity:

In one embodiment, the viscosity measurements are carried out at 6° C. on fermented milks, after storage for 1, 7, 14 and 28 days at 6° C. The apparatus used is an RVFtype Brookfield® viscometer (Brookfield Engineering Laboratories, Inc.) mounted on a Helipath stand (Brookfield Engineering Laboratories, Inc.) The viscometer is equipped with a type C needle and the oscillation speed applied to the needle is 10 rpm. In accordance with the present invention this method is a preferred method for measuring viscosity.

Method to Measure Flow:

In another embodiment, the flow measurements are carried out at 6° C. on fermented milks, after storage for 14 days at 6° C. and which have been previously stirred. The apparatus used is an AR1000-N rheometer (TA Instruments) equipped with co-axial cylinders (Radius 1=15 mm, Radius 2=13.83 mm, Height 32 mm, Air gap=2 mm). For the ascending segment shear stress [Pa] is applied in a continuous sweep from 0 to 60 Pa for a duration of 1 minute according to a linear mode. For the descending segment, the shear stress [Pa] applied in a continuous sweep varies from 60 to 0 Pa for a duration of 1 minute according to a linear mode. The values taken into account are the thixotropic area (Pa/s) and the yield stress (Pa); the latter is calculated according to the Casson model.

In accordance with the present invention, the viscosity of a food, food additive, feed, nutritional supplement, or probiotic supplement may be modified or modulated using the lactic acid bacterium described herein. Preferably, the viscosity is increased.

Bacteriophage

As used herein, the term "bacteriophage" has its conventional meaning as understood in the art ie. a virus that selectively infects one or more bacteria. Many bacteriophages are specific to a particular genus or species or strain of bacteria.

The term "bacteriophage" is synonymous with the term "phage".

The bacteriophage may be a lytic bacteriophage or a lysogenic bacteriophage.

A lytic bacteriophage is one that follows the lytic pathway through completion of the lytic cycle, rather than entering the lysogenic pathway. A lytic bacteriophage undergoes viral replication leading to lysis of the cell membrane, destruction of the cell, and release of progeny bacteriophage particles capable of infecting other cells.

A lysogenic bacteriophage is one capable of entering the lysogenic pathway, in which the bacteriophage becomes a dormant, passive part of the cell's genome through prior to completion of its lytic cycle.

Bacteriophages may include, but are not limited to, bacteriophages that belong to any of the following virus families: Corticoviridae, Cystoviridae, Inoviridae, Leviviridae, Microviridae, Myoviridae, Podoviridae, Siphoviridae, or Tectiviridae.

Advantageously, the lactic acid bacterium according to the present invention is phage resistant.

Over the last 2 decades a library of more than one thousand phages virulent for industrial *S. thermophilus* strains have been collated. This collection of phages was intensively studied and their host spectrum was established. This allowed the identification of a set of 60 phages representative of all the host spectrums identified within the collection of phages. Each of these representative phages was tested on strains DSMZ18344, CNCM I-2423 and CNCM I-2425, as described herein. CNCM I-2423 was found to be sensitive to phage D4126 and D3215. Strain CNCMI-2425 was found to be sensitive to phage D4369. On the contrary strain DSMZ-18344 of the present invention was resistant to all the representative phages tested.

In one embodiment, the lactic acid bacterium of the present invention is resistant to phage D4126 and/or D3215 and/or phage D4369.

In one embodiment, the lactic acid bacterium according to the present invention is resistant to one or more bacteriophage or one or more sets of bacteriophage. In another embodiment, the lactic acid bacterium according to the present invention is resistant to the same bacteriophage that strain CNCM I-2423 and/or CNCM I-2425 are resistant to.

Crispr Locus

As used herein, the term "CRISPR locus" is defined as the DNA segment which includes all of the CRISPR repeats, starting with the first nucleotide of the first CRISPR repeat and ending with the last nucleotide of the last (terminal) CRISPR repeat.

The CRISPR locus is a distinct class of interspersed short sequence repeats (SSRs) that were first recognized in *E. coli* (Ishino et al. (1987) *J. Bacteriol.* 169:5429-5433; Nakata et al. (1989) *J. Bacteriol.* 171:3553-3556). Similar interspersed SSRs have been identified in *Haloferax mediterranei, Streptococcus pyogenes, Anabaena*, and *Mycobacterium tuberculosis* (Groenen et al. (1993) *Mol. Microbiol.* 10:1057-1065; Hoe et al. (1999) *Emerg. Infect. Dis.* 5:254-263; Masepohl et al. (1996) *Biochim. Biophys. Acta* 1307:26-30; Mojica et al. (1995) *Mol. Microbiol.* 17:85-93). The CRISPR loci differ from other SSRs by the structure of the repeats, which have been termed short regularly spaced repeats (SRSRs) (Janssen et al. (2002) *OMICS J. Integ. Biol.* 6:23-33; Mojica et al. (2000) *Mol. Microbiol.* 36:244-246). The repeats are short elements that occur in clusters, that are always regularly spaced by unique intervening sequences with a constant length (Mojica et al. (2000) *Mol. Microbial.* 36:244-246). Although the repeat sequences are highly conserved between strains, the number of interspersed repeats and the sequences of the spacer regions differ from strain to strain (van Embden et al. (2000) *J. Bacterial.* 182:2393-2401).

The common structural characteristics of the CRISPR locus are described in Jansen et al. (2002) as (i) the presence of multiple short direct repeats, which show no or very little sequence variation within a given locus; (ii) the presence of non-repetitive spacer sequences between the repeats of similar size; (iii) the presence of a common leader sequence of a few hundred basepairs in most species harbouring multiple CRISPR loci; (iv) the absence of long open reading frames within the locus; and (v) the presence of one or more cas genes.

CRISPR repeats are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPR repeats are generally homogenous within a given genome with most of them being identical. However, there are examples of heterogeneity in, for example, the Archaea (Mojica et al. 2000).

Advantageously, the CRISPR locus can be used to type and/or screen bacteria.

As will be appreciated by a person skilled in the art, there are numerous different methods for screening/typing a bacterium. In this regard, numerous methods are set forth in, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press.

In one embodiment, amplification is used.

By "amplification" we mean the production of additional copies of a nucleic acid sequence.

Amplification techniques include, but are not limited to, methods broadly classified as thermal cycling amplification methods and isothermal amplification methods.

Suitable thermal cycling methods include, for example, ligase chain reaction (*Genomics* 4:560, (1989); and *Science* 241: 1077 (1988)), the polymerase chain reaction (PCR) (as described in U.S. Pat. Nos. 4,683,195; 4,683,202; and 4,965,188) and Real time PCR; the Polymerase Ligase Chain Reaction (PCR Methods and Applic. (1991) 1:5-16); Gap-LCR (WO 90/01069); the Repair Chain Reaction (EP 439,182); and 3SR (Proc. Natl. Acad. Sci. U.S.A. (1989) 86:1173-1177; Proc. Natl. Acad. Sci. U.S.A. (1990) 87:1874-1878; and WO 92/0880). Isothermal amplification methods include, for example, Strand Displacement Amplification (SDA) (*Proc. Nat. Acad. Sci.* USA 89:392-396 (1992)), Q-beta-replicase (*Bio/Technology* 6:1197-1202 (1988)); nucleic acid-based Sequence Amplification (NASBA) (*Bio/Technology* 13:563-565 (1995)); and Self-Sustained Sequence Replication (*Proc. Nat. Acad. Sci. USA* 87:1874-1878 (1990)).

In a preferred embodiment of the present invention, the amplification method is PCR. This is generally carried out using PCR technologies well known in the art (Dieffenbach and Dveksler (1995) *PCR Primer, a Laboratory Manual* (Cold Spring Harbor Press, Plainview, N.Y.).

As is well known in the art, oligonucleotide primers can be designed for use in amplification reactions to amplify a desired sequence.

By "primer" we mean an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent—such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method. PCR primers are preferably at least about 10 nucleotides in length (e.g. 11, 12, 13, 14, 15, 16, 17, 18 or 19 nucleotides in length), and most preferably at least about 20 nucleotides in length.

Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially mismatched primers, and the like.

Suitably, a bacterium may be screened by amplifying (e.g. PCR amplifying) the CRISPR (e.g. CRISPR1) locus using primers targeting conserved stretches within the leader and trailer (as described in Bolotin et al., (2005) *Microbiology* 151(8):2551-61).

Suitably, a bacterium may be screened by amplifying (e.g. PCR amplifying) selected portions of the CRISPR (e.g. CRISPR1) locus. In this regard, it has been surprisingly found that the *Streptococcus thermophilus* strain described herein lacks 5 CRISPR spacers as compared to, for example, *S. thermophilus* CNCM I-2425 and *S. thermophilus* CNRZ385. In particular, it has been found that the *Streptococcus thermophilus* strain of the present invention lacks the first, second, tenth, eleventh and twelfth CRISPR1 spacers from the 5' end of the CRISPR spacer as compared to, for example, *S. thermophilus* CNCM I-2425 and *S. thermophilus* CNRZ385. As the skilled person will appreciate, this property of the *Streptococcus thermophilus* strain of the present invention can advantageously be used to detect this strain since amplicons of different lengths will be obtained when compared to at least *S. thermophilus* CNCM I-2425 and *S. thermophilus* CNRZ385. So for example, a first primer could be designed to hybridise to the leader sequence at the 5' end of the CRISPR locus and a second primer could be designed to hybridise downstream of the second missing CRISPR spacer sequence and/or downstream of the twelfth missing CRISPR spacer in the *Streptococcus thermophilus* strain of the present invention. By way of further example, a first primer could be designed to hybridise downstream of the second missing CRISPR spacer sequence and a second primer could be designed to hybridise downstream of the twelfth missing spacer.

Preferably, said bacterium is screened using oligonucleotide primers, which specifically or substantially hybridise to said nucleotide sequence(s) as described herein.

In one aspect, there is provided a method for identifying a *Streptococcus thermophilus* strain comprising the use of an oligonucleotide primer which specifically hybridises to the sequence set forth in SEQ ID No. 19 or a homologue thereof with at least 75% identity thereto.

In a further aspect, there is provided a method for identifying a *Streptococcus thermophilus* strain comprising the use of oligonucleotide primers which flank CRISPR spacers that are absent in *Streptococcus thermophilus* DSMZ-18344.

In one embodiment, the forward primer hybridises to one or more of the CRISPR1 spacers labelled C, D, E, F, G, H, or I (see FIG. 3). The reverse primer hybridises to one or more of the CRISPR1 spacers labelled M, N, O, P, Q, or R (see FIG. 3). Suitably, primers do not hybridise to the spacer labelled as S. Typically, the amplified fragment will be about 200 bp shorter with DSMZ18344 as compared to other strains described herein—such as CNCM I-2425.

In a further aspect, there is provided a method for identifying a *Streptococcus thermophilus* strain comprising the use of a forward oligonucleotide primer which hybridises to SEQ ID No. 1 and a reverse oligonucleotide primer which hybridises to the SEQ ID No. 18.

In another aspect, there is provided a method for identifying a *Streptococcus thermophilus* strain comprising the use of a forward oligonucleotide primer which hybridises to SEQ ID No. 1 and a reverse oligonucleotide primer which hybridises to any of SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16 and/or SEQ ID No. 17.

In another aspect, there is provided a method for identifying a *Streptococcus thermophilus* strain comprising the use of a forward oligonucleotide primer which hybridises to any of SEQ ID No. 2, SEQ ID No. 3, SEQ ID No. 4, SEQ ID No. 5, SEQ ID No. 6, SEQ ID No. 7, SEQ ID No. 8 and a reverse oligonucleotide primer why hybridises to any of SEQ ID No. 9, SEQ ID No. 10, SEQ ID No. 11, SEQ ID No. 12, SEQ ID No. 13, SEQ ID No. 14, SEQ ID No. 15, SEQ ID No. 16 and/or SEQ ID No. 17.

In another aspect, there is provided a method for identifying a *Streptococcus thermophilus* strain comprising the use of a forward oligonucleotide primer which hybridises to any of SEQ ID No. 2, SEQ ID No. 3, SEQ ID No. 4, SEQ ID No. 5, SEQ ID No. 6, SEQ ID No. 7 and/or SEQ ID No. 8 and reverse oligonucleotide primer which hybridises to SEQ ID No. 18.

In another aspect, there is provided a method for identifying a *Streptococcus thermophilus* strain comprising the use of a forward oligonucleotide primer which hybridises to any of SEQ ID No. 9, SEQ ID No. 10, SEQ ID No. 11, SEQ ID No. 12, SEQ ID No. 13, SEQ ID No. 14, SEQ ID No. 15, SEQ ID No. 16 and/or SEQ ID No. 17 and a reverse oligonucleotide primer why hybridises to any SEQ ID No. 18.

Preferably, forward and/or reverse oligonucleotide primers that hybridise to SEQ ID No. 15 and SEQ ID No. 16 are not used.

The forward oligonucleotide primer may even hybridise to a sequence that is upstream of SEQ ID No. 2.

The reverse primer may even hybridise to a sequence that is downstream of SEQ ID No. 18.

Following amplification/detection, the amplified sequence may be identified using various methods that are known in the art.

By way of example, the amplified sequence may be identified by determining the amplification product restriction pattern. Accordingly, once the DNA has been amplified, it may be digested (e.g. cut) with one or more restriction enzymes.

As used herein, the term "restriction enzymes" refers to enzymes (e.g. bacterial enzymes), each of which cut double-stranded DNA at or near a specific nucleotide sequence. Restriction enzymes are well known in the art and may be readily obtained, for example, from variety of commercial sources (for example, New England Biolabs, Inc., Beverly, Mass.). Similarly, methods for using restriction enzymes are also generally well known and routine in the art. Restriction enzymes that produce between 10 and 24 fragments of DNA when cutting the CRISPR locus or a portion thereof may be used. Fragments of DNA obtained using restriction enzymes may be detected, for example, as bands by gel electrophoresis. Restriction enzymes may be used to create Restriction Fragment Length Polymorphisms (RFLPs).

RFLPs are generated by cutting ("restricting") a DNA molecule with a restriction endonuclease. Many hundreds of such enzymes have been isolated, as naturally made by bacteria. In essence, bacteria use such enzymes as a defensive system, to recognise and then cleave (restrict) any foreign DNA molecules that might enter the bacterial cell (e.g., a viral infection). Each of the many hundreds of different restriction enzymes has been found to cut (i.e., "cleave" or "restrict") DNA at a different sequence of the 4 basic nucleotides (A, T, G, C) that make up all DNA molecules, e.g., one enzyme might specifically and only recognise the sequence A-A-T-G-A-C, while another might specifically and only recognise the sequence G-T-A-C-T-A, etc. Depending on the unique enzyme involved, such recognition sequences may vary in length, from as few as 4 nucleotides to as many as 21 nucleotides. The larger the recognition sequence, the fewer restriction fragments will result, as the larger the recognition site, the lower the probability that it will repeatedly be found throughout the DNA.

By way of further example, the amplified sequence may be identified by determining or also determining the difference in size of the amplification product, as described above.

Separation may be achieved by any method suitable for separating DNA, including, but not limited to, gel electrophoresis, high performance liquid chromatography (HPLC), mass spectroscopy, and use of a microfluidic device. In one embodiment, the amplification products or DNA fragments are separated by agarose gel electrophoresis. Gel electrophoresis separates different sized charged molecules by their rate of movement through a stationary gel under the influence of an electric current. These separated amplification products or DNA fragments can easily be visualised, for example, by staining with ethidium bromide and by viewing the gel under UV illumination. The banding pattern reflects the sizes of the restriction digested DNA or the amplification products.

By way of further example, the amplified sequence may be identified by sequencing the amplification products.

The sequence of the amplified products may be obtained by any method known in the art, including automatic and manual sequencing methods. See, for example, Sambrook et al. (1989) *Molecular Cloning: A Laboratory Manual* (2d ed., Cold Spring Harbor Laboratory Press, Plainview, N.Y.; Roe et al. (1996) *DNA Isolation and Sequencing* (Essential Techniques Series, John Wiley & Sons).

Preferably, the *Streptococcus thermophilus* that is identified in accordance with the methods of the present invention has substantially the same characteristics as the *Streptococcus thermophilus* strain deposited at DSMZ (Deutsche Sammlung von Mikroorganismen und Zellkulturen GmbH, Mascheroder Weg 1 b, D-38124 Braunschweig) under deposit number 18344 on 14 Jun. 2006. In the context of the present invention, the phrase "substantially the same characteristics" means that the *Streptococcus thermophilus* strain has one or more (preferably all) of the characteristics of the *Streptococcus thermophilus* strain deposited at DSMZ (Deutsche Sammlung von Mikroorganismen und Zellkulturen GmbH, Mascheroder Weg 1 b, D-38124 Braunschweig) under deposit number 18344 on 14 Jun. 2006.

Suitably, the *Streptococcus thermophilus* that is identified is a fast acidifying lactic acid bacterium; and/or the *Streptococcus thermophilus* that is identified generates a viscosity in fermented milk greater than about 62 Pa·s, preferably about 68 Pa·s; and/or the *Streptococcus thermophilus* that is identified is phage resistant; and/or the *Streptococcus thermophilus* that is identified belongs to the genetic cluster CL0189; and/or the *Streptococcus thermophilus* that is identified comprises the sequence set forth in SEQ ID No. 20; and/or the *Streptococcus thermophilus* that is identified comprises the sequence set forth in SEQ ID No. 19 or a variant, fragment, homologue or derivative thereof.

Crispr Orientation

For the avoidance of doubt, in the context of the present invention the CRISPR locus is orientated as follows.

The CRISPR leader is a conserved DNA segment of defined size. For example, the leader sequence of *S. thermophilus* LMG18311 (Accession CP000024) CRISPR1 is the DNA segment starting immediately after the stop codon of gene stu0660, and ending just before the first repeat. The CRISPR leader is located at the 5' end of the CRISPR locus. The CRISPR leader is located immediately upstream of the first CRISPR repeat of the CRISPR locus.

The CRISPR trailer is a conserved DNA segment of defined size. For example, the trailer sequence of *S. thermophilus* LMG18311 (Accession CP000024) CRISPR1 is the DNA segment starting immediately after the terminal repeat, and ending just before the stop codon of gene stu0661 (located on the opposite DNA strand). The CRISPR trailer is located at the 3' end of the CRISPR locus. The CRISPR trailer is located immediately downstream of the terminal repeat.

By way of example, the CRISPR leader and CRISPR trailer sequences in the CRISPR1 locus of *Streptococcus thermophilus* strain CNRZ1066 are:

```
CRISPR leader
5'-CAAGGACAGTTATTGATTTTATAATCACTATGTGGGTATAAAAACG

TCAAAATTTCATTTGAG-3'

CRISPR trailer
5'-TTGATTCAACATAAAAAGCCAGTTCAATTGAACTTGGCTTT-3'
```

The CRISPR leader corresponds to positions 625038 to 625100, and the CRISPR trailer corresponds to positions 627845 to 627885 in the full genome (CP000024) of *Streptococcus thermophilus*.

For the avoidance of doubt "upstream" means in the 5' direction and "downstream" means in the 3' direction.

EPS

Lactic bacteria are known to be capable of producing two classes of polysaccharides in their culture medium, namely homopolysaccharides such as dextrans or levans which consist of the repeated assembly of a single sugar, and heteropolysaccharides commonly called exopolysaccharides or EPSs (EPS is short for the term "exopolysaccharide") consisting of the assembly of several different sugars forming a repeating unit (Cerning J., Bacteries lactiques, [Lactic bacteria], Vol I, by de Roissart H and Luquet F. M., Lorica, 309-329, 1994).

A lactic bacterium producing an EPS can impart a ropy character and/or a smooth and creamy texture to an acidified milk (Cerning et al., FEMS Microbiol., 87, 113-130, 1990). EPSs can also display biological activities which are especially advantageous for human or animal health, such as antitumour or probiotic activities, for example (Oda M. et al., Agric. Biol. Chem., 47, 1623-1625, 1983; EP94870139.6).

Distinct EPS gene clusters have been characterised in *S. thermophilus*. The distribution of regulatory and structural genes within each of these clusters shows a modular organisation that is conserved in other *Streptococcus* spp. Although the function of most EPS-related genes (currently designated eps or cps) and gene products are only inferred from sequence or structural homologies, the 5' region of each cluster appears to encode proteins involved in regulation of EPS synthesis, chain length determination, and membrane translocation. These open reading frames are followed by genes encoding the glycosyl-1-phosphate transferase and glycosyltransferases required for assembly of the basic repeating unit, and enzymes involved in repeat unit polymerization. Finally, the 3' end of these clusters typically contain genes for additional proteins involved in membrane translocation of the polymer subunits, and enzymes needed for the production of sugar nucleotide precursors (e.g., N-acetyl-D-galactosamine; that are unique to the EPS (i.e., not found in other cell polymers).

The first four genes in the 5' region of *S. thermophilus* eps clusters, epsA-D, are highly conserved among this and other EPS+ *Streptococcus* spp appear to contribute regulation (epsA and epsB), polymerization (epsC), and membrane translocation (epsD) functions to EPS synthesis. epsE encodes a glycosyl-1-phosphate transferase that catalyzes the first step in assembly of the EPS basic repeating unit: addition of hexose-1-phosphate to the lipid-phosphate carrier. Genes downstream of epsE appear to encode glycosyltransferases, export/polymerization functions, sugar biosynthesis, and a few enzymes whose function is unknown. Genes encoding a variety of glycosyltransferases have been identified in *S. thermophilus* and other lactic acid bacteria.

The lactic acid bacterium according to the present invention comprises an EPS gene cluster comprising the sequence set forth in SEQ ID No. 20 or a variant, fragment, homologue or derivative thereof.

Surprisingly, the lactic acid bacterium described herein has high eps sequence similarity with *S. thermophilus* CNCM I-2425 from the start of the eps gene cluster sequence up to about position 3900 (ie. in epsE gene) and high eps sequence similarity with *S. thermophilus* CNCM I-2423 from about position 3900 to the end of the sequence.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC). Substantially Suitably, the oligonucleotide primers described herein substantially anneal or substantially hybridise to its respective nucleic acid. This means that an oligonucleotide—such as a primer—should be sufficiently complementary to hybridise or anneal to its respective nucleic acid.

The oligonucleotide sequence need not reflect the exact sequence of its respective nucleic acid, and can, in fact, be "degenerate". Non-complementary bases or other sequences may be interspersed into the oligonucleotide or the nucleic acid, provided that the oligonucleotide sequence has sufficient complementarity with the sequence to permit hybridisation. Thus, by way of example, the primers used for PCR amplification may be selected to be "substantially" complementary to the specific sequence to be amplified.

Starter Cultures

Starter cultures are used extensively in the food industry in the manufacture of products (e.g. fermented products) including milk products—such as yoghurt and cheese.

Starter cultures used in the manufacture of many fermented milk, cheese and butter products include cultures of bacteria, generally classified as lactic acid bacteria. Such bacterial starter cultures impart specific features to various dairy products by performing a number of functions.

Commercial non-concentrated cultures of bacteria are referred to in industry as 'mother cultures', and are propagated at the production site, for example a dairy, before being added to an edible starting material, such as milk, for fermentation. The starter culture propagated at the production site for inoculation into an edible starting material is referred to as the 'bulk starter'.

The bacterial starter culture may consist of the lactic acid bacterium described herein, ie., a pure culture. In this case, substantially all, or at least a significant portion of the bacterial starter culture would generally comprise the same bacterium.

In the alternative, the starter culture may comprise several bacterial strains, ie. it may be a defined mixed culture.

For example, the starter culture may be suitable for use in the dairy industry. When used in the dairy industry the starter culture may additionally comprise a lactic acid bacteria species, a *Bifidobacterium* species, a *Brevibacterium* species, and/or a *Propionibacterium* species.

Cultures of lactic acid bacteria are commonly used in the manufacture of fermented milk products—such as buttermilk, yoghurt or sour cream, and in the manufacture of butter and cheese, for example Brie or Harvati.

Suitable lactic acid bacteria include commonly used strains of a *Lactococcus* species, a *Streptococcus* species, a *Lactobacillus* species including the *Lactobacillus acidophilus*, *Enterococcus* species, *Pediococcus* species, a *Leuconostoc* species and *Oenococcus* species or combinations thereof.

*Lactococcus* species include the widely used *Lactococcus lactis*, including *Lactococcus lactis* subsp. *Lactis*, *Lactococcus lactis* subsp. *lactis biovar diacetylactis* and *Lactococcus lactis* subsp. *cremoris*.

Other lactic acid bacteria species include *Leuconostoc* sp., *Streptococcus thermophilus*, *Lactobacillus delbrueckii* subsp. *bulgaricus* and *Lactobacillus helveticus*. Mesophilic cultures of lactic acid bacteria commonly used in the manufacture of fermented milk products such as buttermilk, yoghurt or sour cream, and in the manufacture of butter and cheese, for example Brie or Harvati. In addition, probiotic strains such as *Bifidobacterium lactis, Lactobacillus acidophilus, Lactobacillus casei* may be added during said manufacturing to enhance flavour or to promote health.

Cultures of lactic acid bacteria commonly used in the manufacture of cheddar and Monterey Jack cheeses include *Streptococcus thermophilus, Lactococcus lactis* subsp. *lactis* and *Lactococcus lactis* subsp. *cremoris* or combinations thereof.

Thermophilic cultures of lactic acid bacteria commonly used in the manufacture of Italian cheeses such as Pasta filata or parmesan, include *Streptococcus thermophilus* and *Lactobacillus delbrueckii* subsp *bulgaricus*. Other *Lactobacillus* species—such as *Lactobacillus helveticus*—may be added during manufacturing to obtain a desired flavour.

The selection of organisms for the starter culture of the invention will depend on the particular type of products to be prepared and treated. Thus, for example, for cheese and butter manufacturing, mesophillic cultures of *Lactococcus* species, *Leuconostoc* species and *Lactobacillus* species are widely used, whereas for yoghurt and other fermented milk products, thermophillic strains of *Streptococcus* species and of *Lactobacillus* species are typically used.

The starter culture may even be a dried starter culture.

The starter culture may be a concentrated starter culture.

The starter culture may be a concentrated starter culture used in direct inoculation.

The starter culture may be a frozen starter culture.

Preparing Starter Cultures

Starter cultures may be prepared by techniques well known in the art such as those disclosed in U.S. Pat. No. 4,621,058. By way of example, starter cultures may be prepared by the introduction of an inoculum, for example a bacterium, to a growth medium to produce an inoculated medium and ripening the inoculated medium to produce a starter culture.

Preparing Dried Starter Cultures

Dried starter cultures may be prepared by techniques well known in the art, such as those discussed in U.S. Pat. Nos. 4,423,079 and 4,140,800.

Dried starter cultures for use in the present invention may be in the form of solid preparations. Examples of solid preparations include, but are not limited to tablets, pellets, capsules, dusts, granules and powders which may be wettable, spray-dried, freeze-dried or lyophilised.

The dried starter cultures for use in the present invention may be in either a deep frozen pellet form or freeze-dried powder form. Dried starter cultures in a deep frozen pellet or freeze-dried powder form may be prepared according to the methods known in the art.

The starter cultures for use in the present invention may be in the form of concentrates which comprise a substantially high concentration of one or more bacteria. Preferably the concentrates may be diluted with water or resuspended in water or other suitable diluents, for example, an appropriate growth medium or mineral or vegetable oils, for use in the present invention. The dried starter cultures of the present invention in the form of concentrates may be prepared according to the methods known in the art, for example by centrifugation, filtration or a combination of such techniques.

Product

Any product, which is prepared from, contains or comprises a lactic acid bacterium is contemplated in accordance with the present invention.

Suitable products include, but are not limited to a food, a foodstuff, a food additive, a food supplement, a feed, a nutritional supplement, a probiotic supplement, a cosmetic product or a pharmaceutical product.

These include, but are not limited to, fruits, legumes, fodder crops and vegetables including derived products, grain and grain-derived products, dairy foods and dairy food-derived products, meat, poultry and seafood.

The term "food" is used in a broad sense and includes feeds, foodstuffs, food ingredients, food supplements, and functional foods. Here, the term "food" is used in a broad sense—and covers food for humans as well as food for animals (i.e. a feed). In a preferred aspect, the food is for human consumption.

As used herein the term "food ingredient" includes a formulation, which is or can be added to foods and includes formulations which can be used at low levels in a wide variety of products that require, for example, acidifying or emulsifying.

As used herein, the term "functional food" means a food which is capable of providing not only a nutritional effect and/or a taste satisfaction, but is also capable of delivering a further beneficial effect to consumer. Although there is no legal definition of a functional food, most of the parties with an interest in this area agree that there are foods marketed as having specific health effects.

The bacteria described herein may be—or may be added to—a food ingredient, a food supplement, or a functional food.

The food may be in the form of a solution or as a solid—depending on the use and/or the mode of application and/or the mode of administration.

The bacteria described here can be used in the preparation of food products such as one or more of confectionery products, dairy products, meat products, poultry products, fish products and bakery products.

By way of example, the bacteria can be used as ingredients to soft drinks, a fruit juice or a beverage comprising whey protein, health teas, cocoa drinks, milk drinks and lactic acid bacteria drinks, yoghurt, drinking yoghurt and wine.

The present invention also provides in a further aspect a method of preparing a food, food additive, feed, nutritional supplement or probiotic supplement, the method comprising admixing the lactic acid bacterium according to the present invention with a food, food additive, feed, nutritional supplement, probiotic supplement and/or food or feed ingredient (such as a starting material for a food).

Preferably a food as described herein is a dairy product. More preferably, a dairy product as described herein is one or more of the following: a yoghurt, a cheese (such as an acid curd cheese, a hard cheese, a semi-hard cheese, a cottage cheese), a buttermilk, quark, a sour cream, kefir, a fermented whey-based beverage, a koumiss, a milk beverage, a yoghurt drink, a fermented milk, a matured cream, a cheese, a fromage frais, a milk, a dairy product retentate, a process cheese, a cream dessert, or infant milk.

Preferably, a food as described herein is a fermented food product. More preferably, a food as described herein is a fermented dairy product—such as a milk beverage, a yoghurt drink, a fermented milk, a matured cream, a cheese, a fromage frais, a dairy product retentate, a process cheese, a cream dessert, or infant milk.

Preferably the dairy product according to the invention comprises milk of animal and/or plant origin.

Milk is understood to mean that of animal origin, such as cow, goat, sheep, buffalo, zebra, horse, donkey, or camel, and the like. The milk may be in the native state, a reconstituted milk, a skimmed milk or a milk supplemented with compounds necessary for the growth of the bacteria or for the subsequent processing of fermented milk, such as fat, proteins of a yeast extract, peptone and/or a surfactant, for example. The term milk also applies to what is commonly called vegetable milk, that is to say extracts of plant material which have been treated or otherwise, such as leguminous plants (soya bean, chick pea, lentil and the like) or oilseeds (colza, soya bean, sesame, cotton and the like), which extract contains proteins in solution or in colloidal suspension, which are coagulable by chemical action, by acid fermentation and/or by heat. Finally, the word milk also denotes mixtures of animal milks and of vegetable milks.

In one embodiment, the term "milk" means commercial UHT milk supplemented with 3% (w/w) of semi-skimmed milk powder pasteurized by heating during 10 min+/−1 min. at 90° C.+/−0.2° C.

In a further aspect there is provided a method for preparing a fermented milk product wherein said process comprises fermenting a milk substrate in the presence of at least the lactic acid bacterium, the culture or the starter culture described herein. Preferably, the milk substrate is milk. Preferably, the milk substrate comprises solid items. Preferably, the solid items comprise or consist of fruits, chocolate products, or cereals.

Sequence

For some embodiments of the present invention, it is preferred that the sequence is a naturally occurring nucleic acid sequence.

The nucleic acid sequence may be DNA or RNA of genomic, synthetic or recombinant origin e.g. cDNA. The nucleotide sequence may be double-stranded or single-stranded whether representing the sense or antisense strand or combinations thereof. Recombinant nucleic acid sequences may be prepared by use of recombinant DNA techniques, as described herein.

The nucleic acid sequence and the nucleic acids encompassed by the present invention may be isolated or substantially purified. By "isolated" or "substantially purified" is intended that the nucleic acid molecules, or biologically active fragments or variants, homologues or derivatives thereof are substantially or essentially free from components normally found in association with the nucleic acid in its natural state. Such components include other cellular material, culture media from recombinant production, and various chemicals used in chemically synthesising the nucleic acids.

An "isolated" nucleic acid sequence or nucleic acid is typically free of nucleic acid sequences that flank the nucleic acid of interest in the genomic DNA of the organism from which the nucleic acid was derived (such as coding sequences present at the 5' or 3' ends). However, the molecule may include some additional bases or moieties that do not deleteriously affect the basic characteristics of the composition.

In one aspect, there is provided the nucleotide sequence set forth in SEQ ID No. 19 or fragment, variant, homologue or derivative thereof.

In a further aspect, there is provided the sequence set forth in SEQ ID No. 19 or a homologue thereof with at least 75% identity thereto.

Suitably, the sequence set forth in SEQ ID No. 19 or a homologue thereof has at least 75% identity thereto, when the full length CRISPR loci are aligned.

Variants/Homologues/Derivatives/Fragments

The present invention encompasses the use of variants, homologues, derivatives and fragments of nucleic acid sequences.

The term "variant" is used to mean a naturally occurring nucleotide sequence which differs from a wild-type sequence.

The term "fragment" indicates that a nucleotide sequence comprises a fraction of a wild-type sequence. It may comprise one or more large contiguous sections of sequence or a plurality of small sections. Preferably the sequence comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence.

Preferably, the fragment retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type nucleotide sequence.

The fragment may be a functional fragment.

By a "functional fragment" of a molecule is understood a fragment retaining or possessing substantially the same biological activity as the intact molecule. In all instances, a functional fragment of a molecule retains at least 10% and at least about 25%, 50%, 75%, 80%, 85%, 90%, 95%, 96%, 97%, 98% or 99% of the biological activity of the intact molecule.

The term "homologue" means an entity having a certain homology with the subject nucleotide sequences. Here, the term "homology" can be equated with "identity".

In the present context, a homologous sequence is taken to include a nucleotide sequence, which may be at least 60, 70, 75, 85 or 90% identical, preferably at least 95%, 96%, 97%, 98% or 99% identical to the subject sequence. Although homology can also be considered in terms of similarity, in the context of the present invention it is preferred to express homology in terms of sequence identity.

Homology comparisons may be conducted by eye, or more usually, with the aid of readily available sequence comparison programs. These commercially available computer programs can calculate % homology between two or more sequences.

% homology may be calculated over contiguous sequences. This is called an "ungapped" alignment. Typically, such ungapped alignments are performed only over a relatively short number of residues.

Most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, *Nucleic Acids Research* 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410), the GENEWORKS suite of comparison tools and CLUSTAL. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix—such as BLOSUM62.

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used:

| FOR BLAST | | | |
|---|---|---|---|
| GAP OPEN | | 0 | |
| GAP EXTENSION | | 0 | |

| FOR CLUSTAL | DNA | PROTEIN | |
|---|---|---|---|
| WORD SIZE | 2 | 1 | K triple |
| GAP PENALTY | 10 | 10 | |
| GAP EXTENSION | 0.1 | 0.1 | |

The nucleotide sequences may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences may be modified by any method available in the art. Such modifications may be carried out to enhance the in vivo activity or life span of nucleotide sequences useful in the present invention.

Vector

The nucleotide sequence(s) described herein may be present in a vector. The nucleotide sequence may be operably linked to regulatory sequences such that the regulatory sequences are capable of providing for the expression of the nucleotide sequence by a suitable host organism ie. the vector may be an expression vector.

The term "expression vector" means a construct capable of in vivo or in vitro expression.

Preferably, the expression vector is incorporated in the genome of the organism. The term "incorporated" preferably covers stable incorporation into the genome.

The vectors may be transformed into a suitable host cell as described below to provide for expression of a polypeptide having the specific properties as defined herein.

The choice of vector, e.g. plasmid, cosmid, virus or phage vector, will often depend on the host cell into which it is to be introduced.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Constructs

The term "construct"—which is synonymous with terms such as "conjugate", "cassette" and "hybrid"—includes a nucleotide sequence directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention, which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct comprises at least a nucleotide sequence operably linked to a promoter.

Host Cells

The term "host cell" includes any cell that comprises a nucleotide sequence, a construct or a vector.

The cells will be chosen to be compatible with the said vector and may for example be prokaryotic (for example bacterial), fungal, yeast or plant cells. Preferably, the host cells are not human cells.

Examples of suitable bacterial host organisms are gram negative bacterium or gram positive bacteria.

General Recombinant DNA Methodology Techniques

The present invention employs, unless otherwise indicated, conventional techniques of biochemistry, molecular biology, microbiology and recombinant DNA, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

Further Aspects

In a further aspect, there is provided a lactic acid bacterium comprising the sequence set forth in SEQ ID No. 20 or a variant, fragment, homologue or derivative thereof, preferably, a homologue thereof with at least 99% identity thereto.

In a further aspect, there is provided a nucleotide sequence comprising the sequence set forth in SEQ ID No. 20 or a variant, fragment, homologue or derivative thereof, preferably, a homologue thereof with at least 99% identity thereto.

In a further aspect, there is provided a method for identifying a lactic acid bacterium comprising the step of screening a bacterium for the sequence set forth in SEQ ID No. 20 or a variant, fragment, homologue or derivative thereof, preferably, a homologue thereof with at least 99% identity thereto.

In a further aspect, there is provided a micro-organism a *Streptococcus thermophilus* strain deposited under the Budapest Treaty by Danisco Deutschland Niebüll GmbH, Buch-Johannsen Strasse.1, Niebüll-D-25899, Germany at DSMZ (Deutsche Sammlung von Mikroorganismen and Zellkulturen GmbH, Mascheroder Weg 1 b, D-38124 Braunschweig) under deposit number 18344 on 14 Jun. 2006 or a mutant or variant thereof having one of or more of the characteristics of the deposited *Streptococcus thermophilus* strain.

The invention will now be further described by way of Examples, which are meant to serve to assist one of ordinary skill in the art in carrying out the invention and are not intended in any way to limit the scope of the invention.

EXAMPLES

Example 1

*Streptococcus thermophilus* DSMZ-18344 is a Fast Acidifier of Milk

The speed of acidification of milk during the fermentation process is −0.0153 upH/min, compared to 0.0129 upH/min, 0.0167 upH/min and 0.0209 upH/min for *Streptococcus thermophilus* CNCM I-2423, *Streptococcus thermophilus* CNCM I-2980 and *Streptococcus thermophilus* CNCM I-2425, respectively.

Example 2

*Streptococcus thermophilus* DSMZ-18344 Generates Fermented Milk with a Superior Viscosity Fresh fermented milks are produced at lab scale. The milk base is composed of commercial UHT milk supplemented with 3% (w/w) semi-skimmed milk powder. After mixing, the milk base is heated during 10 min+/−1 min at 90° C.+/−0.2° C. The base is then cooled down at 43° C.+/−1° C. in a water bath regulated at 43° C.+/−1° C. and the milk is dispatched into 125 ml glass beakers.

The milk is inoculated with the bacterium at a ratio of 1E6-1E7 cfu/ml. The fermentation is carried out at 43° C.+/−1° C. with out stirring and it is stopped when the pH reaches 4.6+/−0.05. At this moment, the fresh fermented milk is quickly cooled down at 6° C.+11° C. in less than 1 hour. Finally, the products are stored at this temperature during 28 days.

Following this production of fermented milk either viscosimetry is measured using a Brookfield viscosimeter.

The viscosity in fermented milk is 68 Pa·s after 14 days of storage at 6° C.

Usually a strain identified as highly texturizing generates fermented milk with a viscosity superior to 45 Pa·s, a Casson yield stress inferior to 12.0 Pa and a thixotropy area inferior to 1000 Pals.

A comparison of the rheological properties of three texturizing S. thermophilus strains are shown in Table 1.

Example 3

Molecular Analysis of Streptococcus thermophilus DSMZ-18344

The EPSAD PCR-RFLP method is a molecular method to establish genetic lineage between strains of S. thermophilus.

Streptococcus thermophilus genomic DNA is purified using the DNeasy Tissue Kit (Qiagen). Purified DNA is then amplified by PCR with the following parameters:
Composition of the PCR reaction mix (50 µL):
buffer for DNA polymerase×1
MgCl$_2$ 2 mM
dNTP 200 µM each
genomic DNA 100 to 500 ng

```
primer EPSA632
(5'-AAATgAATTCAgAgCAAgCACTTg-3')  200 nM primer EPSD1064
(5'-gTCATgTCAACTTTATTAAggACg-3')  200 nM
```

DNA polymerase 1.25 unit
H$_2$O qsp 50 µL
Amplification parameters:
predenaturation at 94° C. during 1 min
35 cycles with denaturation at 94° C. during 30 s, hybridization at 56° C. during 30 s, elongation at 72° C. during 3 min
post-elongation at 72° C. during 6 min.

After amplification, the PCR product is checked by 1.5% agarose gel electrophoresis. The size of the amplification product is about 2.5 kb.

The PCR product is then digested by two restriction enzymes FokI et MnlI in the following conditions:
PCR product 15 to 30 µL
buffer 2 (New England Biolabs)×1
BSA (New England Biolabs)×1
FokI (New England Biolabs) 1 unit
MnlI (New England Biolabs) 1 unit
H2O qsp 50 µL
Incubation at 37° C. during 1 hour.

The digested product is analysed by 3% agarose gel electrophoresis.

Applied to S. thermophilus DSMZ-18344, it groups this strain within a genetic cluster known as CL0189. This was further confirmed by the sequencing of the proximal part of its eps operon (that is the targeted chromosomal region with the EPSAD method).

The EPSAD PCR-RFLP profile of S. thermophilus DSMZ-18344 is shown in FIG. 1.

Referring to this Figure, S. thermophilus DSMZ-18344 shows genetic lineage to S. thermophilus CNCM I-2425 profile which is the representative strain of the CL0189 genetic cluster.

The distal part of the eps operon was also sequenced and compared to that available in the literature. Unexpectedly, this part of the S. thermophilus DSMZ-18344 eps operon is distinct to that of strain S. thermophilus CNCM I-2425. However, it is very similar to that of S. thermophilus CNCM I-2423 and other strains within the S. thermophilus CNCM I-2423 genetic cluster (namely CL0089 that also contains S. thermophilus CNCM I-2426 and S. thermophilus Sfi39 (Genbank entry AF373595).

Figure 2:
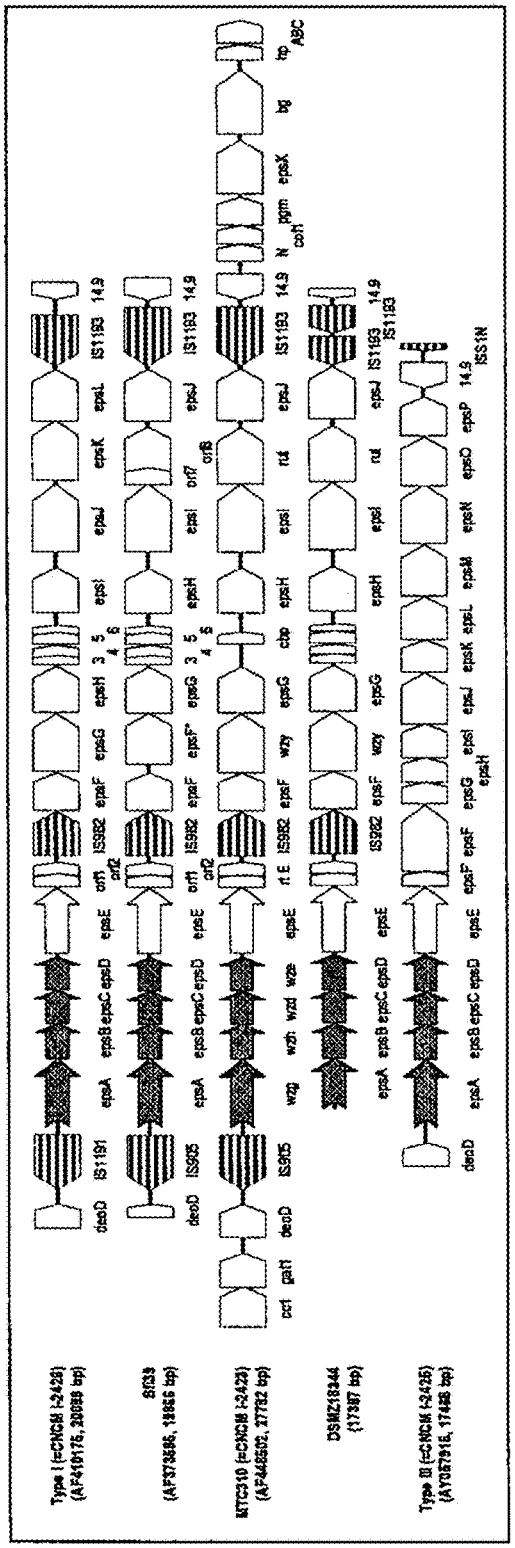

Schematic organisation of the distal part of the eps operon and similarities between strains are shown in FIG. 2.

The sequence data on the distal part of the eps operon and the EPSAD clustering data together suggest that the eps operon of S. thermophilus DSMZ-18344 is a chimeric operon made of the proximal part of the operon coming from S. thermophilus CNCM I-2425 (or related strains) and the distal part of the operon coming from S. thermophilus CNCM I-2423 (or related strains).

This unusual feature may be useful to develop a method to specifically detect S. thermophilus DSMZ-18344 (or related strains from other S. thermophilus) as described herein.

The strain S. thermophilus CNCM I-2423 is one of the fast acidifying strains that presents texturizing properties of interest in fermented milk whereas S. thermophilus CNCM I-2425 even if fast acidifying does not have these interesting texturing properties. In S. thermophilus, the distal part of the eps operon contains genes that code for glycosyl transferases. These enzymes are known to be responsible of the structure of the polysaccharidic units composing the exopolysaccharide and the nature of this exopolysaccharide is at least partly believed to be responsible of the texturizing properties of a strain. Therefore, the chimeric structure of the eps operon may explain its texturing capabilities.

Example 4

CRISPR Spacers of S. thermophilus DSMZ-18344

The spacer sequences in the CRISPR locus are genetic features that are very specific to a strain or to related strains.

The spacers of the CRISPR 1 locus of S. thermophilus DSMZ-18344 have been sequenced and compared to that of S. thermophilus CNCM I-2425, S. thermophilus CNCM I-2423 and other spacer sequences. The only similarities were found with S. thermophilus CNRZ385 (Genbank accession number DQ072992) and CNCM I-2425 (and related strains). Interestingly, the spacers within this CRISPR locus have a different organisation (5 missing spacers) and 1 additional spacer were identified.

The lysotype of S. thermophilus DSMZ-18344 and the differences observed between the lysotype of S. thermophilus DSMZ-18344 and strains of the CL0189 genotype are shown in Table 2.

Example 5

S. thermophilus DSMZ-18344 is Phage Resistant

Over the last 2 decades a library of more than one thousand phages virulent for industrial S. thermophilus strains have been collated. This collection of phages was intensively studied and their host spectrum was established. This allowed the identification of a set of 60 phages representative of all the host spectrums identified within the collection of phages.

Each of these representative phages was tested on strains DSMZ18344, CNCM I-2423 and CNCM I-2425, as described herein.

CNCM I-2423 was found to be sensitive to phage D4126 and D3215. Strain CNCMI-2425 was found to be sensitive to phage D4369. On the contrary strain DSMZ-18344 was resistant to all the representative phages tested.

TABLE 1

| Strain name | Viscosity (Pa · s) | Casson yield stress (Pa) | Thixotropy area (Pa/s) |
| --- | --- | --- | --- |
| DSMZ-18344 | 68 | 6.48 | 627 |
| CNCM I-2425 | 28 | 14.43 | 21780 |
| CNCM I-2423 | 49 | 9.28 | 1035 |

TABLE 2

| Strain | Genotype | Distal part of eps operon | Sensitivity to CNCM I-2425 phages | Sensitivity to CNCM I-2423 phages | Sensitivity to other phages | Texturing |
| --- | --- | --- | --- | --- | --- | --- |
| DSMZ-18344 | CL0189 | CNCM I-2423 type | No | No | No | Yes |
| CNCM I-2423 | CL0089 | CNCM I-2423 type | No | Yes | No | Yes |
| CNCM I-2425 | CL0189 | CNCM I-2425 type | Yes | No | No | No |

SEQUENCES (5'-3')

SEQ ID No. 1
*S. thermophilus* DSMZ-18344 CRISPR1 sequence leader sequence
actatgtgggtataaaaacatcaaaatttcatttgag SEQ ID No. 2
*S. thermophilus* DSMZ-18344 CRISPR1 spacer (1)
aatatctacaggtcactacaaagctacgct SEQ ID No. 3
*S. thermophilus* DSMZ-18344 CRISPR1 spacer (2)
gttggggtgtgtttgtaacggcgtatgcta SEQ ID No. 4
*S. thermophilus* DSMZ-18344 CRISPR1 spacer (3)
tcaatcaggtgacggtgatgcttatattaa SEQ ID No. 5
*S. thermophilus* DSMZ-18344 CRISPR1 spacer (4)
catacatgatagtttgtcaacacttttgat SEQ ID No. 6
*S. thermophilus* DSMZ-18344 CRISPR1 spacer (5)
tcagcatttggtttacatgacccacgtctg SEQ ID No. 7
*S. thermophilus* DSMZ-18344 CRISPR1 spacer (6)
caatcaacaggtttgactgattataacggt SEQ ID No. 8
*S. thermophilus* DSMZ-18344 CRISPR1 spacer (7)
tagctacacatgaattttattacaatggtg SEQ ID No. 9
*S. thermophilus* DSMZ-18344 CRISPR1 spacer (8)
ccgtt cttcaaacgttaaattccaaggtgt SEQ ID No. 10
*S. thermophilus* DSMZ-18344 CRISPR1 spacer (9)
gctgcgattatgacaatgctgtctgtaagg SEQ ID No. 11
*S. thermophilus* DSMZ-18344 CRISPR1 spacer (10)
gaagaatttattaataaagatggttctgct SEQ ID No. 12
*S. thermophilus* DSMZ-18344 CRISPR1 spacer (11)
aggcagaaaagaagtattttggtaagtatg SEQ ID No. 13
*S. thermophilus* DSMZ-18344 CRISPR1 spacer (12)
aaatggtttatcgacaagaaaatgaagct SEQ ID No. 14
*S. thermophilus* DSMZ-18344 CRISPR1 spacer (13)
ccaaatttgcattatacaaaacgctccttc SEQ ID No. 15
S. thermophilus DSMZ-18344 CRISPR1 spacer (14)
atcctaactgctttgctaactacatcatgg SEQ ID No. 16
S. thermophilus DSMZ-18344CRISPR1 spacer (15)
atcctaactgctttgctgactacatcatgg SEQ ID No. 17
S. thermophilus DSMZ-18344 CRISPR1 spacer (16)
taacaagataagattagtcgtcttctacat SEQ ID No. 18
S. thermophilus DSMZ-18344 CRISPR1 sequence trailer sequence
ttgattcaacataaaaagccagttcaattgaacttggcttt SEQ ID No. 19
S. thermophilus DSMZ-18344 CRISPR1 sequence
actatgtgggtataaaaacatcaaaatttcatttgaggttttttgtactctcaagatttaagtaactgta caacaatatctacaggtcactacaaagctacgctgtttttgtactctcaagatttaagtaactgtacaa cgttggggtgtgtttgtaacggcgtatgctagttttttgtactctcaagatttaagtaactgtacaac tcaatcaggtgacggtgatgcttatattaagttttttgtactctcaagatttaagtaactgtacaaccat acatgatagtttgtcaacacttttgatgttttttgtactctcaagatttaagtaactgtacaactcagca tttggtttacatgacccacgtctggttttttgtactctcaagatttaagtaactgtacaaccaatcaaca ggtttgactgattataacggtgttttttgtactctcaagatttaagtaactgtacaactagctacacatg aattttattacaatggtggttttttgtactctcaagatttaagtaactgtacaacccgttcttcaaacgt taaattccaaggtgtgttttttgtactctcaagatttaagtaactgtacaacgctgcgattatgacaatg ctgtctgtaagggttttttgtactctcaagatttaagtaactgtacaacgaagaatttattaataaagat ggttctgctgtttttgtactctcaagatttaagtaactgtacaacaggcagaaaagaagtattttggta agtatggttttttgtactctcaagatttaagtaactgtacaacaaatggtttatcgacaagaaaatgaag ctgttttttgtactctcaagatttaagtaactgtacaacccaaatttgcattatacaaaacgctccttcg tttttgtactctcaagatttaagtaactgtacaacatcctaactgctttgctaactacatcatgggttt ttgtactctcaagatttaagtaactgtacaacatcctaactgctttgctgactacatcatgggttttttg tactctcaagatttaagtaactgtacaactaacaagataagattagtcgtcttctacatgttttttgtac tctcaagatttaagtaactgtacagtttgattcaacataaaaagccagttcaattgaacttggcttt SEQ ID No. 20
S. thermophilus DSMZ-18344 EPS gene cluster
gctgagccagcttactagcgtacaggcacctactaaggttgataagaacaatatcgaggt cttgatgtcagctctcaaaaaagataaaaaagttgatgttaaagttgatgatgttgcttc atatcaagaagcttatgataatctcaagtctggcaaatctaaagctatggtcttgagtgg ctcttatgctagcctattagagtctgtcaatagtaaccttgcttcaaatctaaaaacaat ttatacttataaaattaaaaagaagaataacaactctgcaaaccaagtagattcaaaagt cttcaatatttatattagtggtattgatacctacggttcgatttcaacagtgtcacgttc agatgtcaatattattatgacagtaaacatgaatacacataagattctcttgacgactac tccacgtgatgcatacgttaagattcctggtggtggggcaaaccagtatgataaattaac ccacgcaggtatttatggtgttgaaacatctgaacaaactctggaagatctatatggtac taagattgattactatgcacgaattaacttcacatctttccttaagttgattgaccaact tggtggtgtgacagtccataatgatcaagctttcacaagtcttcatgggaagtttgattt cccagttggagatatccaaatgaattcagagcaagcacttggatttgttcgtgaacgcta tagtttagatggcggagataatgaccgtggtaaaaaccaggagaaagtcatttctgcgat tgtaaacaagttggcttctctaaagtctgtatcaaactttacttcaatcgttaataatct -continued

```
ccaagactctgttcagacaaatatttctttggataccattaatgctttggctaatacaca acttgattcaggctctaaatttacagtaacgtctcaagcagtaactggtacaggttcaac cggacaattgacctcttatgcgatgccaaattctagtctttacatgatgaaactagataa ttcgagtgtggcaagtgcctctcaagctatcaaaaatctgatggaggaaaaataagtgat tgacgttcactcacatattgtttttgatgttgatgatggtcctaaaactttagaagaaag tttagacctcattggtgaaagttatgcccagggggtacgtaagattgtttcaacatccca tcgtcgtaaggggatgtttgagactccagaggataaaattttgccaacttttctaaggt aaaagcagaagcagaagcactttatccagacttaactatttattatggaggtgaacttta ttacaccctagacattgtggagaaacttgaaaagaatctcattccgcgcatgcacaacac tcaatttgctttgattgagtttagtgctcgcacatcttggaaagaaattcatagtgggct tagtaatgttttgagagcgggggtaacgcctattgttgctcatattgagcgctatgatgc cctcgaagaaaatgctgatcgtgttagagaaattatcaatatgggctgctatactcaagt caatagctcacatgtcctcaaaccaaagctctttggagataaagaaaaagtaagaaagaa acgtgttcgcttttcttggagaaaaatttggttcatatggttgctagcgacatgcataa tcttgggccgagaccaccatttatgaaagatgcttatgaaattgttaaaaagaactacgg ctccaaacgtgctaagaatcttttttattgaaaatcccaaaacattactagaaaatcaata tttataggagatattatgaatcaagataacactaaaagtgatgaaatcgacgtactagca ttgctacataaactttggacgaagaagcttttgattcttttcacagcttttatttcgct gctttcagtttcttaggtacttatttctttatccaaccaacatatacatcaacaacgctt atctatgttgttaatcaggcaacagataataataatctttctgctcaagatttgcaagct ggtacctatttggcaaatgactataaagagattattacatcaaatgatgtattatcagaa gttattaaagatgaaaaattgaatttgagtgaggcagaactgtctaaaatggtttcagtt aatattcctactgatactcgtcttatttcaatttctgttaatgctaaaactggtcaagat gcgcaaacacttgctaataaggttcgtgaagttgcttcaaaaaaaatcaagaaggtgaca aaagttgaagatttcacaatgctcgaagaagctaaattgccagagtcaccatcttcacca aatatcaaacttaatgtgcttcttggggcagtgcttggaggattccttgcagtggttggt gtattggtacgtgaaatcctagatgatcgtgttcgccgtccagaagatgtggaagatgcc cttggaatggcacttcttggaattgtccctgatacagataaaatttaaggagaagaaatg cctctattaaagttagtaaaatctaaagtaaactttgccaaacaaacagaagagtattac aatgccattcgcacaaatattcaattttctggtgctcagattaaagtgattgcgattagc tctgttgaagctggtgaaggaaaatcaacgacatctcttaacttggcgatttcatttgct agtgttgggctccgaacacttctgattgatgctgatactcgtaattctgttttttcaggt acatttaaatcaaatgagccttataaaggtctttcaaattttctttcaggaaatgccgat ctaaatgaaacgatttgccaaactgatatttctggtttggatgttattgcatctggtcct gttccacctaatccaacaagtcttttgcaaaatgacaattttagacatttgatggaagtt gctcgtagtcgttatgattatgtcatcatcgatacaccaccagttggtttggttattgat gcagttattattgcccatcaggctgatgccagtcttttggttacagcagctgggaaaatc aaacgtcgtttcgtaactaaggccgtcgaacaattggaacaaagtggttctcagttctta ggtgtcgtccttaataaagttgacatgacagttgataaatatggatcatatggttcttac ggatcatatggttcttacggatcatatggtgagtacaggaaaaaacagaccaaactgaa ggtcattcaagagcacatcgtcgtagaaaaggatagcattaatggggatgatgcggctcc
```

-continued

```
ttataccttaacagattaaaaaggggtttagagtgaaagaaaaacaagaaattcgtcgca ttgaaattggtattatacagttggttgtggttgttttcgcagccatggtagctagtaaaa taccatatacagagattacccaaggaagtattgtccttttaggtgtcgtacatgtagtgt cttactatatcagtagttattatgaaaatcttaagtatagaggctacttggatgaactca ttgcaactgtcaaatattgtttcatatttgctctaattgcaacatttctctcgttttttg cagatggaagttttcaatctcacgtcgcggacttctttacgtcaccatgatttcaggtg ttctcttatacgttacaaatactgttcttaagtatttccgctcatctatttatacacgtc gtaaaagtaacaagaatattctcttgatttctgatcaggcacgtcttgataatgttttgt ctcgtatgaaagacaatatggatggtaggattacagcagtttgtgtcttggataatcctt attttactgatccatttatcaagagtgttaaacctgaaaatttgattgaatatgcgacac actcagtagtagaccaagttttgattaatctgccaagtgggcagtataagatttgggatt atgcatcaccttttgagatcatgggaattccagtttctattaatttgaatgcccttgaat ttatgagtcaaggtgaaaaacgtattcaacaatgggtcctttcaaagttgttacgtttt caacgcaattttatagctatggagatatcttggcgaaacgtttcctcgatatctgtggag ccctagttggtttggtgctctgtgggattgttggaatcttcctttatccacttattcgta aggatggtgggccagccattttttgctcaagaccgtgtgggagaaaatggacgtatcttta agttttataaattccgttctatgtgtgttgatgcggaagaaatcaagaagaatttgatgg cacagaatcaaatgtctggtggtatgtttaagatggacaatgatccacgtattaccaaaa ttggacgtttcattcgtaaaacaagtcttgatgaacttccacaattttggaatgtcctaa aagtgatatgagcttggttgggacacgtcctccaacagttgatgagtatgaaaaatata cacctgaacagaaacgtcgtttaagttttaaacctggtatcactggtctttggcaagtaa gcggtcgaagtgaaattactgattttgatgaagttgtaaaactagacgttgcttatttgg acggatggacaatctggcgtgatatcaaaatcttattgaaaacaattaaagtagtagtaa tgaaggatggagcaaagtgatggctttcaccatttctttaatggtgattaaatgacaaa aacagtttatatcgttggttctaaggggattccagcaaaatggtggatttgagacctt tgttgagaagttgacagagttccaacaagacaaagatatccaatattatgtagcttgtat gcgggaaaactctgcaaaatcagacattacagcagatgattttcaaacttcgcaacagaa ccctaaaaagaactccctaacggtcgtggctactttgtttagtctaaacactttgaatag tcctacaagctcatagtttccctttattagttggtccaaggccaattctattttttgaa gcgaaagaatatggggagcgccttccttatttactgatatgtaaacctggaattactggt tattggacgacacatggtcgaagtaaagttctttttcctcaacgagcagatttagaactc tattatctccaatattacagcaccaagaacgacatcaagcttctaatacgtacaatttca caaatcattaacggattggacgcttactaaaaaattaatgaaaaaatatttgaaatcata actcgaaaaatattaaaagattagatatgtatcataaaacccgaattgctagttaatttc attggaaaataaataagtcgtgctatcctaatcttaaaccactaagcattagaaagcgca cgacttatatgacttataatagcacacttccaaaagttttttgtttatttactgacaacca ttgagacgctttatcaaacgagtgttccccttgaggttcaaaaccgaaagaacgtccatc tcgcaacatcagattgcttagttatcgcttgttacctatggggcgtactgcattttagtg aaacgcttaaagcaaagcaccaattggctcaaagtttatttcctaatttcctagaatatt ctcactttgtccgccgttgtaatgccctcttaccgagtatccaagtcattcgccaagcac tcgtatttaaagaggttgaaggaattagtgtatccattattgacagcttccccattcctt
```

-continued

```
tgtgtcagtctattcgtaatttcagaagcaaagttcttggagattatgcaaatgttggct
acaatgctacaaagggacagtacttctatggatgtaaatgtcatgctttagtcagtgaat
caggctatgtcatagactacacaattactcctgcttcaatggctgatagttcaatgaccg
aggaagtgttgagtcaatttgggacaccaacagtccttggagatatgggatatttaggtc
agtcactgcatgataggctggaattaaaaggaattgatctaattacacctgtcaggaaga
acatgaagcaaagaaaattcttttccctaattttcaaaacgtagaaaagtgattgagc
gagttttctctttttttgacaaatctaggagctgagcgttgtaaaagtcgttcgcctcaag
gttttcaattgaaattagagatgatacttttagcgtattctttactgttaaaatcagcta
aatcactggaaccagagactttaagatattctatcgggtatcaagtcatggctaaataat
caactagcaattcgggtatcataaggagtgatttaatgaaaaaaattacaatagcagtt
gcaacgcataaaaaatatcaaatgccaaaagataatatttatctaccaattgaatgtgga
gcagttttaagaaaaaatcacctagactatattgctgatgatagtggagataatatttct
gaaaaaacaagaattattcagagttaacagcactatattggttatggaaaaataatgat
tctgagtataaaggattagcacactatagacgtcattttcagataaaaaggtgagtatt
ttttctacaggtaattttgataatatacttgataggacggtacttgaggaacatttagag
aagtttgatattatacttcccaagcttcgacattactatattgaaacaatagaatctcac
tataaacatacgcattttgaaaaagatttattagcaacagaagaaataattaaaaaacta
tatcctgactatcttgatttttattatagtgcactaaaaagaaaatctgctcatatgttt
aatatgtttattatgaaagataaatatttcaataattattgtgaatggttattttcgatt
cttttgaattagaaaagtactagatatttcagaatattctcccttcatgcaagagta
tttggtcgtgtgagtgaaattttattagatgtatggattttcaagaataatttaaattc
actgaaattccagttatgtttatggaaaagcaaaattggtgggataaatctaaagattt
atttctgcaaagcttttcaacaaaaaatattattagactaggagaaataaattgcttaca
atcggaataattttaataatttttatgactattttcgattattatatacataaaacagta
ttttctccggtctttatgtttaattcactcttttattaataatatctctttcttctatg
aggttatataatttgagagaatattctatcaaatcaatagaagtaattgtgttagggatg
atattcttctcttaggagtattttgtactcgtattgtttctcatgaattttaaaaat
caaaataatgttattaattacgatgataatttaaatgtaaattggactttttaaaaatt
cttttgatagttgtaaccacaggaaacgtattctctattattttttccttgaaattcctt
ttaggaggaggttcatacttagaattgagaaatatgatattgggatataatggagctgaa
ccacttattacgaatcctctcgtaaatatattaacaagatatatcgggaccagggttg
actgctttgatcccattttctattttttttctaattaggaaaaaaaacattaaattttcc
ttaattattttattgaatcttgtttggcaacattatcatccggtggtagaattttactt
gtatatactattattcaattgtttataggattatcttattcaaaaaaaaatataccaaaa
aaaattaagaaagtagtcataatatcaagtattatattttttatatctataattgtctta
tctaacatcagaagttctaacagtatatatagagcgttttatgcatacttttcgggccct
gtagttcttttatctacttggatgactgatgttgatacttataatattcattcacatgga
ttaggatttatttatcccatcacatatctattaaattcattttgtaatttaataggaatt
cctaactcgatgttggctaatgttgtcatgtggcaaggaatgcctcagaatgattgggta
ggcgtattccctaatcaatcgatgaacgcttttagtacacttttctatttttctataaa
gattttcgagaatttggagttgcttgcttttctttccttttgggagtatttgtggtttt
```

-continued

```
atttattttaaagcgtttatcgaaagaaaaagtaaatatctagtctattatttattaggg gtacaggcaattatcggatcttttattatttggcaattggggagtactgcgttttcta agtattgtatttacaatattaagtctgaaatcaaagaaatcataactatagaaaaggaga taaaatatgacaatcagcatagtaatcccagtttataatgttcaagattacataaaaaag tgtctagattctatattaagccagacattttcagatttagaaattattcttgttgatgat ggttctactgacttgagtggaagaatttgtgattattattccgaaaatgataaacgtatt aaagtaatccacacagcaaatgggggacagtcggaagcaaggaacgttggaatcaaaaat gccacatcagaatggataacatttattgattctgatgactacgtttcttctgattatata gagtatttatataatttgattcaagtacacaatgcagatatttcaatagctagttttacc tatatcacacctaaaaagataattaagcacggtaacggtgaagtagctcttatggatgca aaaactgcaattcggagaatgttactgaatgaaggtttcgatatgggagtttgggggaaa atgtatcgaacggagtattttaataaatataaattcgtttcaggaaaactatttgaagat tctttaattacataccagatattttcagaagcttcaacaattgttttggagcaaaggat atttattttatgttaacaggaaaaattctactgttaatggtacttttaatataaaaaag tttgatcttattgaaatgaatgaagaagcaaataagtttattaaacataaatttccagat ctttcatctgaagcacatcgtcgaatgatatgggcatattttagtacactaaatcaagtt ttatcatcaactaatgaacacgatattgatttatatgcgccacaattagtagcttatctc cttaaacaggataaattcataaaaaggaatacttttattcccaaaagagataagattgca ttttttattttaaaaattttggtttaaagacatatcgtaatgtttggaatttatattta aaaatgacaagataaaaacaataatgaaagataaaaaataatgaaaactgctacaattac tttacattcagcacataataatggatctatcttttctacagtcatttgctttgcagagaa agataatatctatgggatatgataacgaaattataaattatattccactcaaattgctcg tagttttaagaaccaagtgcaaaagattattaaggttaacaacgttacgattgttgctac ggccgcaacgccgaagaagccgctgaatacgttgattgggctagttgtcggcttgctata ggatttgtttatgcagcgattcggatgctcacggatcgccgcgttcacgaagctgatttc ttaactgatgaattaggattgactagtttaggcttggttaaccatcaacatcaccattca atgaagaaacaggccttgaatctgaacggtggctatcatacgcataacgatcaaacatct tcacaagcgatgaaacgagtttaggagggtgctagatgtttaaacgtaaagaaaagaata taacgactacggcaccaattaatctcaccacgattaatgaacccatgtcggtcattactg agcagattaaaacaattcgaaccaatatcaattttgcggctactgaccataagctacgaa ctttgatggtgacttcggccatgcttggcgagggtaaatcgacagtaagtggtaacttag cagtggagtatgccaaggaaggaaggcaagcaagtcttactggtcgatgctgacttgcga cgaccaacgattcataagacatttggccttaaaaaccataagggattaagttcatggtta gccaatcagattgacgatgtgaatgatgcaattcatcccgtcattggcaatctataattg tataaatagtatgtatactttataacaatggagtgttttaatgaatcttttgtttagtca atgtcacattacattgaaaatttaaaaaatgtaacttttttgcgtgtgaatagctatgta caatgattttctgggtggcagactaatcaagtataaaatagcttatactagttgacaaca tcccgtgataattattaacttatcaagtacaggccaaaatactggagcttaacaggaact gttagaatatgattttatataattaggagtagaataaagagatgaatccattaatatcaa ttattgttccaacatataatgttgaaaaatatattaggacatgtattgaatcaatcttag ctcaaacatatcgcaatattgaagtcattatagtaaatgatggtagcacagatcagtcgc
```

-continued

```
tagcagtaatttccgatttaatctgtagtcatcataatattaaggtaatcaaccaaaaaa accaaggattatcagtagctcgaaacactggtattgatgcggcaactggtaaatatatag cttttgtagatgcagatgacaaaattaagccagactttgttagctcgctctatcaaattg ctgacaaaacaggagctgacattgtgcgtgggtcatttcgagactttaatggcaatattc ctaaaggctgggttccagatttcaatgttccaaccaattatgggacaatagtattagacc aattcttatccagcaacatatcttttgtagtttggtcgagtatctataggctagattttta ttaatagtaatcatatacgatttacaccagggattctatttgaggatgcagattttacaa taagagcttatatgctcgctaagttagttgctacatcacctgaaccaaattatgcatata gaataaatcgtccaggaagtatattaaccacaaaaaccacaaaaaatgcccaaaaaatgt ctctttcagaagaaaaaattatatcacaatttattagtatgttaaagcatgaaaaatctg atgttttatgtagtttaattctaaagtctatttatgcatgtatgagagattggacgggaa ttattgtgaggaataacctatcgttggataggaagaacagttgttttgatactgctctca ctctaataaaagaataataaattctaggcccttaaaagaaaaaatcaaattttttaacaa aggttattattattaaggcgaaaaaccattaagccgttaaacgaaaatccaagggttca tatacaattatgttaattatggattttttatatcttcaatgggttcattaatcactgaat ttgattatcttgttttaatgaatgtgaagtcattcggttaaggggagtctttgatttgtc tagttagctatctggacagatgttaagtgttaattacagtgaaggcagatgaaaacttat taaaagttattctgcttgattaagaatggtaagatttcaccatctatatacttttattag aacttaggtggacaggaggacccaattttttaatccttcctgttatatagttttttgtttaa tattttttcgggaggattattaatgcaaatagtaaaaaattatcttttataatgcaatgtat caggtctttataattattgtgccattacttaccattccttatttgtcaagaattttgggc ccttcaggtattggaattaactcatataccaattctattgttcagtattttgttttattt ggtagtataggagtcggtttgtatgggaatcgtcagattgcctttgttagggataatcag gtcaaaatgtctaaagtcttttatgaaatatttattttaagactattaacaatatgttta gcatatttattgttcgttgctttttttaaccattaatggtcagtatcatgaatactatttg tttcaatccattgctatagttgcagctgcatttgatatctcttggttttttatgggaatt gaaaattttaaagtaactgtattaagaaattttatagttcagttacttgctctattcagt attttcctatttgtcaaatcttacaatgatttgaatatatatatattgataacagttttta tctacattaattggtaattttaacttttttcccaagtttacacagatatctcgtaaaggtt aactatcgtgaattaaggccaataaagcatttaaagcaatctttagttatgtttatccca caaattgctgtccaaatttattgggttttgaataaaacaatgttaggttcattggattct gtcacgagctccggcttttttgatcagtctgataaaatagttaaactggttttggctatt gctagtgcaacaggtactgtcatgttgccacgtgttgcaaatgcctttgcacatagagag tatagtaaaattaaggagtacatgtacgcaggttttctttttgtgtcggcaatttcgatt cctatgatgtttggtctgatagctattactcctaaattcgtgccacttttttttacatct caatttagtgatgttattcctgtgttaatgatcgagtcaattgcaattattttttatagct tggagcaacgcaataggtaatcaatatcttttaccaactaatcaaaataagtcatataca gtgtcggtgttcattggagcgatagtcaatttaatgttaaatattccactgattatatat ctaggtgctgttggtgcatcaattgcaactgtaatttctgaaatgtctgtaactgtgtat caacttttataattcataaacagcttaatttgcatacactgttttcggatttatctaag tatttaattgcaggattagtgatgtttctaattgtctttaaaattagtttgttaacaccg
```

-continued

```
acatcttggatattcattctgttggaaattactgtgggcataattatttatgttgtttta ttaatattttaaaggcagaaataattaataaactaaagtttattatgcataaatagagg tatggatttaggtacctgcctttaggattttaattcaaaggatttaggtacttatggtt actttaattcgattgtgacctactttattcttttggcaactttaggtgttgctaactatg gtactaaagagatttcaggacatcgaaaggatattcgtaaaaatttctggggtatttata ccctccaattgattgcgactattttgtctcttgtcttgtatacatcattatgtttgttct ttcctggtatgcaaaatatggtggcttatatcttaggattaagcttgatatcgaaggaa tggatatttcttggttattccaaggtttggaggattttcgtcgtattaccgcaaggaata caacggtaaaggttttaggagttatttctatcttcctatttgtgaaaacacctggtgatt tgtatctctatgttttcctattgaccttctttgaattgcttgggcaattaagtatatggt taccagcgagaccttacattggaaaaccacaatttgatttatcctatgctaagaaacatc ttaaacctgttattttgctgtttctccctcaggttgccatttcactatacgtgactttgg atcgtacaatgttgggtgccttgtcatcgacaaatgatgtagggatttatgatcaggctt tgaaaataattaatattttgttgacgttggtgacttcattgggaagtgtaatgcttccaa gggtatctggtcttttatctaacggagatcataaggccgttaacaagatgcatgaattct cttctctgatttataatcttgtgattttcccgataatagcaggtctcttgattgttaata aggattttgtgagtttcttactagggaaagatttccaagaggcttatcttgccattgcta ttatggtctttaggatgttctttatcggttggacaaatattatgggaatccagattttga ttccatataataaacatcgtgagttcatgctctctacgactattccggctgttgtcagtg ttggacttaatctcttgttaatttcctccatttggctttgttggggtctcaattgtatca gttttaacagaggctttggtatgggttattcaattgaattttcaaggatattcatcaaa gatgtgtcaatccttccagccatatcaaaaattatcttagcatcagttgtcatgtatctt ggactctttgtctttaagatgtttgtgcaattgaaaccaatgctaaatgtagcagtagat ggtcttgtcggtgctatcatttatattgtcttgattattgtcttacgtgtcgttgatatg aaagacttgaagcaacagttaatgaaaaactaaggagaaaaatatgtacgattatcttat cgttggtgctggtttgtccggagcaatcttcgcacatgaagctacaaaacgtggcaaaaa agtaaaagtgattgacaagcgtgatcacattggtggcaatatctactgtgaagatgttga aggtattaatgttcacaagtatggtgctcacattttccatacctcaaataaaaaagtttg ggattatgtcaaccaatttgctgaatttaataactatatcaactcaccaattgctaacta caagggcagtctttataaccttccatttaacatgaatacattttatgctatgtgggcac taagactcctcaagaagttaaggacaagattgctgaacaaacggctgatatgaaagatgt tgagcctaaaaacttggaagaacaagctatcaagttgattggaccagatatctacgaaaa gttgatcaagggatacactgaaaaacaatggggacgttctgccacagacctgcctcctt catcatcaagcgtcttccggttcgtctaacttttgataacaactacttaatgaccgtta ccaaggaattccgatcggtggttacaatgtcatcattgaaaatatgcttggagatgtaga agtagagcttggagttgacttctttgccaatcgtgaagagcttgaagcttcagctgaaaa agttgtctttacaggaatgattgaccagtactttgattataaacatggtgagttggagta tcgcagtcttcgttttgaacacgaagtcttggatgaagaaaatcatcaaggaaatgccgt ggtcaactacacagagcgtgagattccttatactcgtatcattgagcataagcacttcga gtatggtacacaacctaagacagttatcacacgtgaatacccagctgattggaaacgtgg agatgaaccatactacccaatcaatgatgaaaagaacaatgccatgtttgctaagtacca
```

-continued

```
agaagaagctgagaaaaatgacaaggttatcttctgtggacgtcttgcagattataaata ctacgacatgcacgtggtcattgagcgtgctctagaagtcgttgagaaagaatttattta ataaataatggctctttgtcaactgtagtgggtgacgaaaagctaacatctagagaggac cggataggtcctctttttatgtatgttcagtgtgatgaagacacgtttcttaaagttgat gaagtttctaaaaccgaagcccaaccgtttgatgtctttgatcaacttattagtcgcttc aagttttgcgtttggatagtccgttctagtgcgtttttgatgtattgcttgtgtctaag aaaagtcctaaagacagtttgaaaatagtgattgaccttgctcctattttcctctatcag gtcaaagaactcatctactctcttctcctgaaagtgaaaaagcaaaagctgataaagtgt atagtagtcagtaagctcttttgaaaagactagtgtcttcgcaacaacttcatgtggtgc taaagtttggcggaaagtcttttgaataaaaagaattgagagatagtttacagctgtcctt ttggaagagtcgccagtgattttcaaggctcgatagggtagtgacttcttatcgaatta gttcatgattgcaattctagtcttaaaaatgctctaccaaggtgctggatgatgtggaa acgatcaagaacgattttgcgtttggaaagagtctgcgggctagtgggataagctcc agacttatccatcgtgataaactgtacctgttatcggactttcaatggatacttcaaaag tagtttcgtatagtagtttggcggcgattatcaaggatggttatgagttggtttgtctca taattctgcgccacaaaagccaattccctttcttgaacccaaactcatcccaggacata acagcagggagtttgtcataatgtttcttgaaagtaaactgatcaagcttacgatagaca gtggacgtcgacacacgaagtcttcttgcaatatcagttagtgacactttctcagttagg agttgtgtaacttttgttggactagattggagatttggtagtttttctcaacgatagat gtctcagctaccgtgactctcctacaatttttacactggaaacgacgttttttcagacgt agtagagttggcgttcccgcttgctcgagaagagggatttagattttttttgaaagtca tatttgatcatctttctttggcagtgaggacatgatggtgtagggtaatcaagttttgct tgaatctcgatatgagtgtcagtttcaaaaacaagtgaaataatgatattttggtcttta actccgattaattctgtggtattcttaataggtctcataagttcttcctaatggtagttt cgtcgcttttcattatagttcttatgggacttttgtgtacactcaaaaagctctataat ctctacagtggttttactcactacagaaattatagagccaatatatctcctgtctatttt tatgctacttttgggttagctcaactcaaccgccttttaatctcccaacaacaataatac cctatcaaacaacccaaaaaattcaagataatatcactaatggcaaatgtgcccaaataa aagataaattgaatggtttcaattcctaaaagtgtgaccaaactgataatgacaaactgt ttgaaattagtattgatacagtaaaggccacctaaaggaatgaagta
```

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry, microbiology and molecular biology or related fields are intended to be within the scope of the following claims.

The invention claimed is:

1. A method for preparing a food, food additive, feed, nutritional supplement, or probiotic supplement, wherein:
    the method comprises adding a fast acidifying *Streptococcus thermophilus* lactic acid bacterium,
    the *Streptococcus thermophilus* lactic acid bacterium comprises the sequence set forth in SEQ ID No. 19 or a homologue thereof with at least 90% identity thereto or a fragment comprising at least 90% of the sequence set forth in SEQ ID No. 19,
    the *Streptococcus thermophilus* lactic acid bacterium further comprises an EPS operon as set forth in in SEQ ID No. 20 or a homologue thereof with at least 99% identity thereto, and
    the *Streptococcus thermophilus* lactic acid bacterium generates a viscosity in fermented milk greater than about 62 pascal-seconds (Pa·s) after 14 days of storage at 6° C.

2. The method according to claim 1, wherein said lactic acid bacterium generates a viscosity in fermented milk greater than about 65 pascal-seconds (Pa·s) after 14 days of storage at 6° C.

3. The method according to claim 1, wherein said lactic acid bacterium further comprises the sequence set forth in SEQ ID No.20.

4. The method according to claim 1, wherein said lactic acid bacterium comprises a homologue of SEQ ID No. 19 with at least 95% identity thereto.

5. The method according to claim 1, wherein said lactic acid bacterium is the *Streptococcus thermophilus* strain deposited at DSMZ (Deutsche Sammlung von Mikroorganismen and Zellkulturen GmbH, Mascheroder Weg 1 b, D -38124Braunschweig) under deposit number 18344 on 14 Jun. 2006 or a mutant thereof and/or a variant thereof, wherein said mutant or variant generates a viscosity in fermented milk greater than about 62 pascal-seconds (Pa·s)

after 14 days of storage at 6° C., wherein said mutant or variant comprises the sequence set forth in SEQ ID No. 19 or a homologue thereof with at least 90% identity thereto or a fragment comprising at least 90% of the sequence set forth in SEQ ID No. 19.

6. The method according to claim 1, wherein said food is a fermented milk product, and wherein said fast acidifying *Streptococcus thermophilus* lactic acid bacterium is added to a milk substrate before said milk substrate is fermented.

7. The method according to claim 1, wherein said lactic acid bacterium is added as a pure culture.

8. The method according to claim 1, wherein said lactic acid bacterium is added as a mixed culture.

9. The method according to claim 8, wherein said mixed culture comprises one or more further lactic acid bacteria selected from the genera consisting of *Streptococcus, Lactococcus, Lactobacillus, Leuconostoc, Pediococcus* and *Bifidobacterium*.

10. The method according to claim 9, wherein said mixed culture comprises one or more further lactic acid bacteria selected from the species consisting of *Lactobacillus delbrueckii* subsp. *bulgaricus, Lactobacillus acidophilus, Lactobacillus casei* and/or a *Bifidobacterium* sp.

11. The method according to claim 1, wherein said lactic acid bacterium is the *Streptococcus thermophilus* strain deposited at DSMZ (Deutsche Sammlung von Mikroorganismen and Zellkulturen GmbH, Mascheroder Weg 1 b, D-38124 Braunschweig) under deposit number 18344 on 14 Jun. 2006.

12. The method according to claim 1, wherein said lactic acid bacterium comprises a homologue of SEQ ID No. 19 with at least 96% identity thereto.

13. The method according to claim 1, wherein said lactic acid bacterium comprises a homologue of SEQ ID No. 19 with at least 97% identity thereto.

14. The method according to claim 1, wherein said lactic acid bacterium comprises a homologue of SEQ ID No. 19 with at least 98% identity thereto.

15. The method according to claim 1, wherein said lactic acid bacterium comprises a homologue of SEQ ID No. 19 with at least 99% identity thereto.

16. The method according to claim 1, wherein said lactic acid bacterium comprises SEQ ID No. 19.

17. A food, food additive, feed, nutritional supplement, or probiotic supplement obtained or obtainable by the method of claim 1.

18. A food, food additive, feed, nutritional supplement, or probiotic supplement according to claim 17, wherein the food, food additive, feed, nutritional supplement, or probiotic supplement is a dairy, meat or cereal food, food additive, feed, nutritional supplement, or probiotic supplement.

19. A dairy food, food additive, feed, nutritional supplement, or probiotic supplement according to claim 18, wherein the dairy food, food additive, feed, nutritional supplement, or probiotic supplement is a fermented milk, yoghurt, cream, matured cream, cheese, fromage frais, a milk beverage, a processed cheese, a cream dessert, a cottage cheese or infant milk.

20. A fermented milk product obtained or obtainable by the method of claim 6.

* * * * *